United States Patent
Allison et al.

(10) Patent No.: US 12,064,174 B2
(45) Date of Patent: Aug. 20, 2024

(54) SYSTEMS AND METHODS FOR TISSUE ABLATION AND MEASUREMENTS RELATING TO THE SAME

(71) Applicant: Hepta Medical SAS, Paris (FR)

(72) Inventors: Robert C. Allison, Rancho Palos Verdes, CA (US); John McCarthy, Newbury, NH (US); Tim Lenihan, Hradek Kralove (CZ)

(73) Assignee: Hepta Medical SAS, Paris (FR)

( * ) Notice: Subject to any disclaimer, the term of this patent is extended or adjusted under 35 U.S.C. 154(b) by 286 days.

(21) Appl. No.: 17/161,147

(22) Filed: Jan. 28, 2021

(65) Prior Publication Data
US 2021/0236202 A1 Aug. 5, 2021

Related U.S. Application Data

(60) Provisional application No. 63/112,101, filed on Nov. 10, 2020, provisional application No. 62/968,726, filed on Jan. 31, 2020.

(51) Int. Cl.
*A61B 18/18* (2006.01)
*A61B 17/00* (2006.01)
*A61B 18/00* (2006.01)

(52) U.S. Cl.
CPC .............. *A61B 18/1815* (2013.01); *A61B 2017/00725* (2013.01); *A61B 2018/00023* (2013.01);
(Continued)

(58) Field of Classification Search
CPC ...... A61B 18/1815; A61B 2017/00725; A61B 2018/00023; A61B 2018/00178;
(Continued)

(56) References Cited

U.S. PATENT DOCUMENTS

| 4,190,053 A | 2/1980 | Sterzer |
| 5,344,435 A | 9/1994 | Turner et al. |

(Continued)

FOREIGN PATENT DOCUMENTS

| CN | 205073020 U | 3/2016 |
| EP | 2299540 B1 | 1/2013 |

(Continued)

OTHER PUBLICATIONS

PCT Partial International Search Report dated Apr. 26, 2021 in Int'l PCT Patent Application Serial No. PCT/IB2021/050682.
(Continued)

*Primary Examiner* — Khadijeh A Vahdat
*Assistant Examiner* — Abigail M Ziegler
(74) *Attorney, Agent, or Firm* — Greenberg Traurig, LLP; Christopher C. Bolten; Albert K. Heng

(57) ABSTRACT

An exemplary ablation system is provided. The system is designed for safe and efficacious energy delivery into tissue by, for example, emitting energy in a controlled, repeatable manner that allows for feedback and energy emission titration based on sensed parameters (e.g., tissue temperature) measured during ablation. The system may include a switching antenna for both heating of target tissue and radiometry to monitor the temperature of the heated tissue. For example, the switching antenna may include a monopole formed by proximal and distal radiating elements, such that the proximal radiating element includes a short to defeat a choke action of the proximal radiating element. The system further includes a processor for calculating the temperature of the target tissue and estimating volume of the ablation lesion based on the target tissue temperature.

26 Claims, 32 Drawing Sheets

(52) U.S. Cl.
CPC .............. *A61B 2018/00178* (2013.01); *A61B 2018/00541* (2013.01); *A61B 2018/00577* (2013.01); *A61B 2018/00642* (2013.01); *A61B 2018/00702* (2013.01); *A61B 2018/00714* (2013.01); *A61B 2018/00791* (2013.01); *A61B 2018/00797* (2013.01); *A61B 2018/00916* (2013.01); *A61B 2018/1853* (2013.01); *A61B 2018/1861* (2013.01); *A61B 2018/1892* (2013.01)

(58) Field of Classification Search
CPC ........... A61B 2018/00577; A61B 2018/00642; A61B 2018/00702; A61B 2018/00714; A61B 2018/00797; A61B 2018/00916; A61B 2018/1853; A61B 2018/1861; A61B 2018/1838
See application file for complete search history.

(56) References Cited

U.S. PATENT DOCUMENTS

| | | | |
|---|---|---|---|
| 7,699,841 | B2 | 4/2010 | Carr |
| 7,769,469 | B2 | 8/2010 | Carr et al. |
| 8,926,605 | B2 | 1/2015 | McCarthy et al. |
| 8,932,284 | B2 | 1/2015 | McCarthy et al. |
| 8,961,506 | B2 | 2/2015 | McCarthy et al. |
| 9,226,791 | B2 | 1/2016 | McCarthy et al. |
| 9,277,961 | B2 | 3/2016 | Panescu et al. |
| 9,861,440 | B2 | 1/2018 | Van Der Weide et al. |
| 9,872,729 | B2 | 1/2018 | Van Der Weide et al. |
| 9,956,038 | B2 | 5/2018 | Allison |
| 11,622,807 | B2 | 4/2023 | Crozier et al. |
| 2004/0243004 | A1 | 12/2004 | Carr |
| 2004/0249272 | A1* | 12/2004 | Carr .................. A61B 18/18 600/430 |
| 2006/0121873 | A1* | 6/2006 | Ammar ................ G01K 11/006 374/E11.003 |
| 2012/0029359 | A1* | 2/2012 | Sterzer ................ A61B 5/0507 600/407 |
| 2013/0041365 | A1* | 2/2013 | Rusin .................... A61B 18/18 606/33 |
| 2013/0281851 | A1 | 10/2013 | Carr |
| 2013/0317499 | A1* | 11/2013 | Brannan ............ A61B 18/1206 606/46 |
| 2013/0324993 | A1* | 12/2013 | McCarthy ............... A61B 5/01 606/33 |
| 2013/0345693 | A1* | 12/2013 | Brannan ............ A61B 18/1815 439/502 |
| 2014/0303614 | A1 | 10/2014 | McCarthy et al. |
| 2016/0030111 | A1 | 2/2016 | Ladtkow et al. |
| 2016/0345896 | A1 | 12/2016 | Allison |
| 2017/0105798 | A1 | 4/2017 | Allison |
| 2017/0172655 | A1 | 6/2017 | Allison et al. |
| 2018/0078309 | A1 | 3/2018 | Van Der Weide et al. |
| 2018/0125579 | A1 | 5/2018 | Van Der Weide et al. |
| 2019/0365466 | A1 | 12/2019 | Allison |
| 2020/0305974 | A1* | 10/2020 | Brannan ................ A61B 34/20 |
| 2022/0125511 | A1 | 4/2022 | Crozier et al. |

FOREIGN PATENT DOCUMENTS

| | | | |
|---|---|---|---|
| EP | 2777591 | A1 | 9/2014 |
| EP | 3456279 | A1 | 3/2019 |
| JP | 2022089125 | A | 6/2022 |
| WO | WO-2006127847 | A2 | 11/2006 |
| WO | WO-2007025198 | A2 | 3/2007 |
| WO | WO-2010048334 | A1 | 4/2010 |
| WO | WO-2010085329 | A1 | 7/2010 |
| WO | WO-2010085529 | A1 | 7/2010 |
| WO | WO-2012007854 | A1 | 1/2012 |
| WO | WO-2013192553 | A1 | 12/2013 |
| WO | WO-2014025549 | A1 | 2/2014 |
| WO | WO-2014138410 | A1 | 9/2014 |
| WO | WO-2015004420 | A1 | 1/2015 |
| WO | WO-2016033090 | A1 | 3/2016 |
| WO | WO-2016054156 | A1 | 4/2016 |
| WO | WO-2016089887 | A1 | 6/2016 |
| WO | WO-2016197093 | A1 | 12/2016 |
| WO | WO-2017173523 | A1 | 10/2017 |
| WO | WO-2017181182 | A1 | 10/2017 |
| WO | WO-2018140816 | A1 | 8/2018 |
| WO | WO-2019231936 | A1 | 12/2019 |
| WO | WO-2020033998 | A1 | 2/2020 |
| WO | WO-2020033999 | A1 | 2/2020 |
| WO | WO-2020188249 | A1 | 9/2020 |
| WO | WO-2022051654 | A1 | 3/2022 |

OTHER PUBLICATIONS

International Search Report and Written Opinion dated Aug. 26, 2019 in Int'l PCT Patent Appl. Serial No. PCT/US2019/034226.
U.S. Appl. No. 16/424,414, filed May 28, 2019.

* cited by examiner

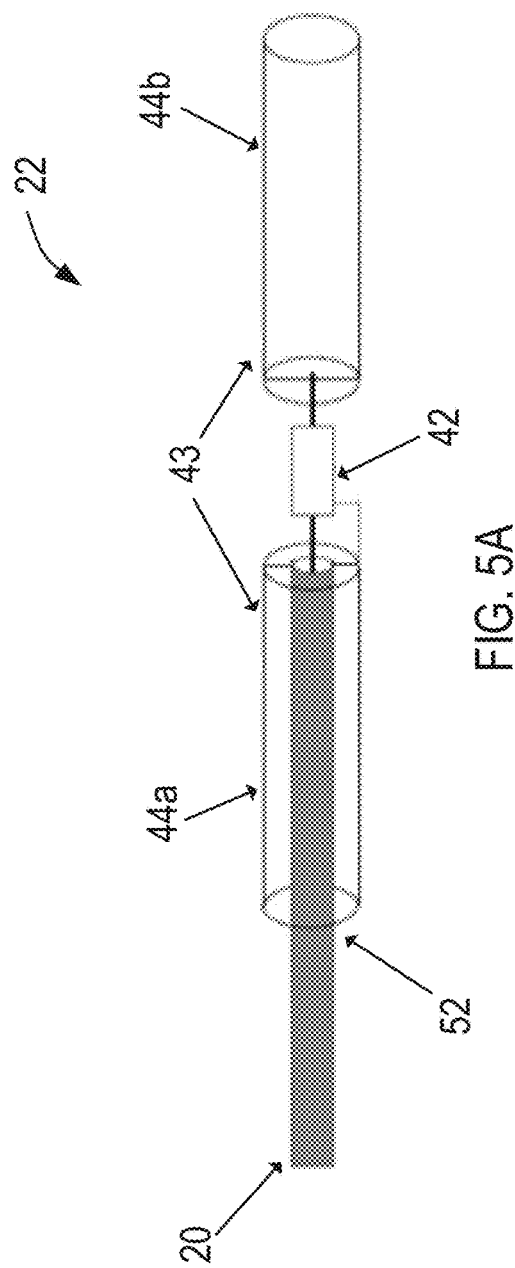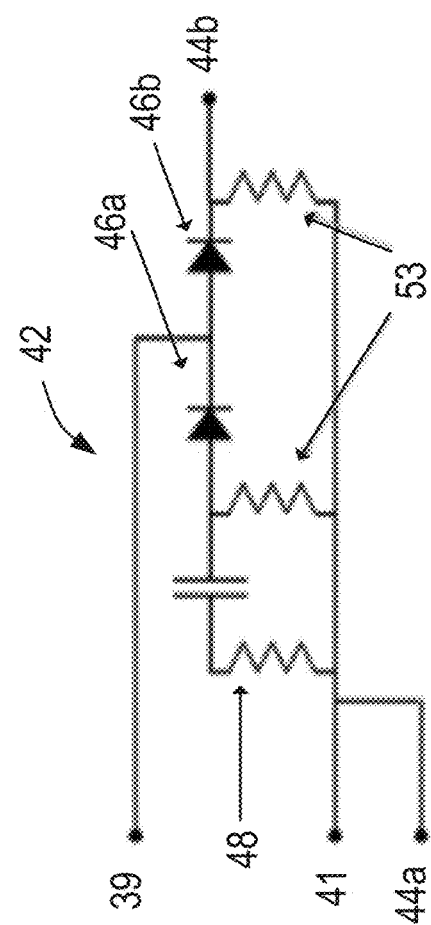
FIG. 5A
FIG. 5B

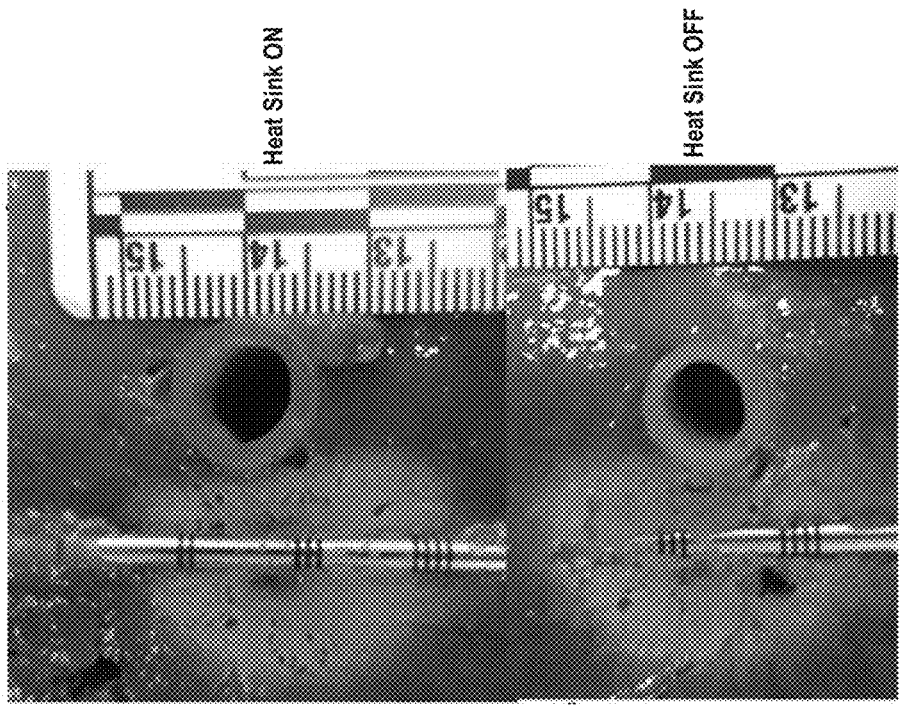
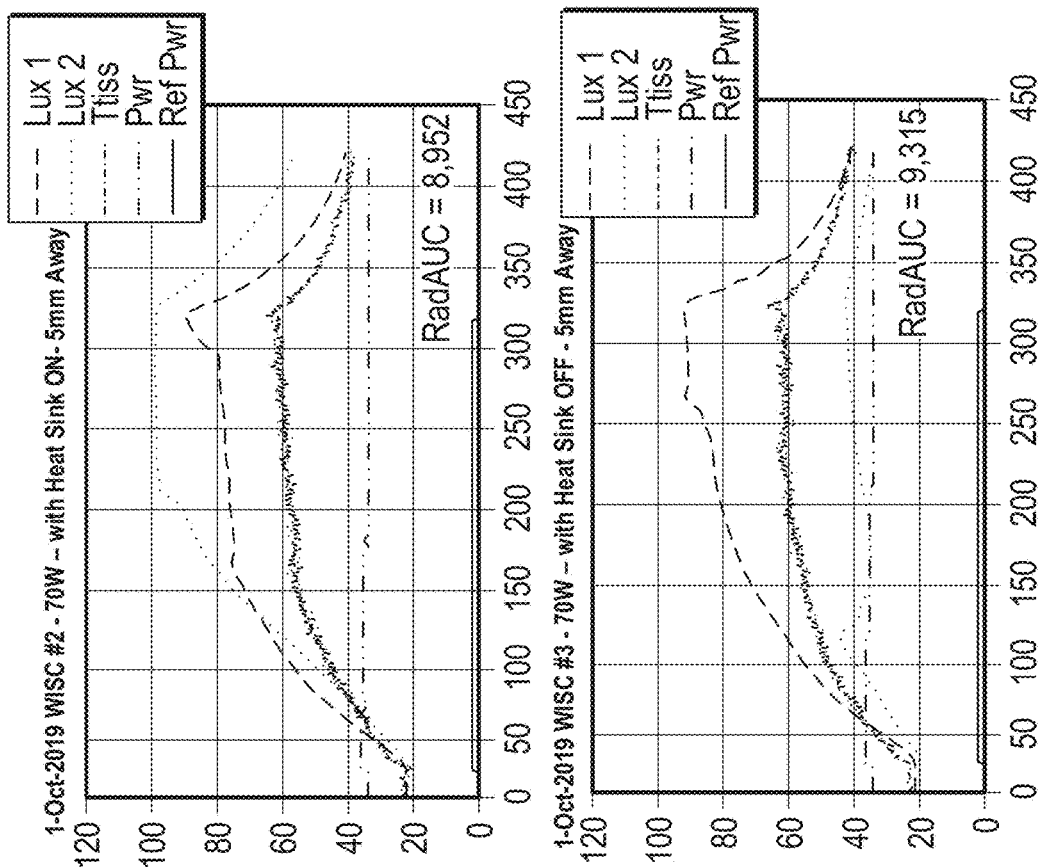
FIG. 21B

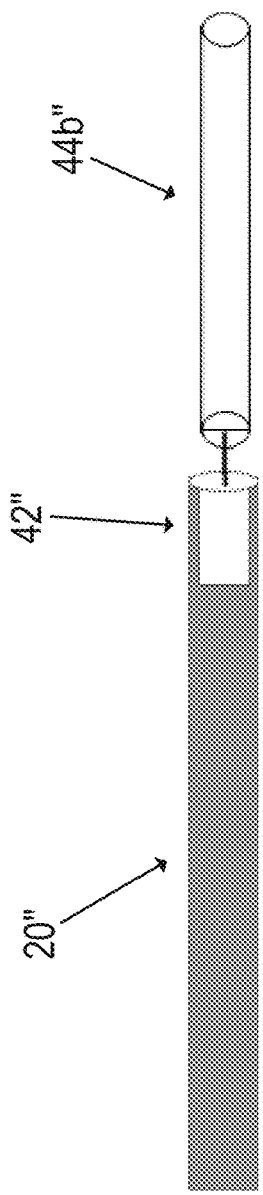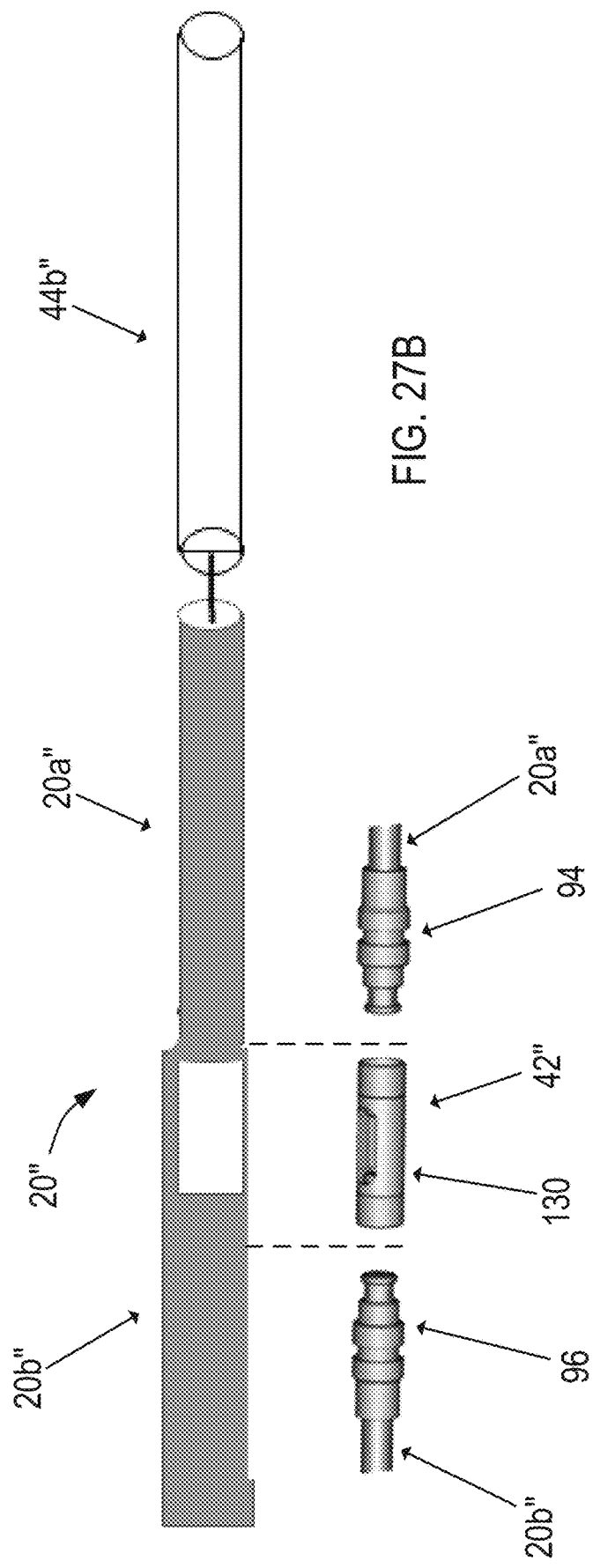

SYSTEMS AND METHODS FOR TISSUE ABLATION AND MEASUREMENTS RELATING TO THE SAME

CROSS-REFERENCE TO RELATED APPLICATIONS

This application claims priority to U.S. Provisional Patent Application No. 63/112,101, filed Nov. 10, 2020, and U.S. Provisional Patent Application No. 62/968,726, filed Jan. 31, 2020, the entire contents of each of which are incorporated herein by reference.

FIELD OF THE INVENTION

This application generally relates to systems and methods for safe and efficacious ablation of target tissue by, for example, measuring parameters during ablation such as temperature of the target tissue, as well as estimating volume of the ablation lesion based on the measured parameters.

BACKGROUND OF THE INVENTION

Tissue ablation may be used to treat a variety of clinical disorders and several ablation techniques have been developed, including cryoablation, microwave ablation, radio frequency (RF) ablation, and ultrasound ablation. Numerous treatment schemes affect the nerve using RF power applied by a catheter contacting the inside wall of the artery.

Such techniques are typically performed by a clinician who introduces a catheter having an ablative tip to the target tissue via the venous vasculature, positions the ablative tip adjacent to what the clinician believes to be an appropriate region based on tactile feedback, mapping electrocardiogram (ECG) signals, anatomy, and/or fluoroscopic imaging, actuates flow of an irrigant to cool the surface of the selected region, and then actuates the ablative tip for a period of time believed sufficient to destroy tissue in the selected region.

Although commercially available ablative tips may include thermocouples for providing temperature feedback via a digital display, such thermocouples typically do not provide meaningful temperature feedback during irrigated ablation. For example, the thermocouple only measures surface temperature, whereas the heating or cooling of the tissue that results in tissue ablation may occur at some depth below the tissue surface. Moreover, for procedures in which the surface of the tissue is cooled with an irrigant, the thermocouple will measure the temperature of the irrigant, thus further obscuring any useful information about the temperature of the tissue, particularly at depth. As such, the clinician has no useful feedback regarding the temperature of the tissue as it is being ablated or whether the time period of the ablation is sufficient.

Accordingly, it may only be revealed after the procedure is completed, that the targeted aberrant pathway was not adequately interrupted. In such a circumstance, the clinician may not know whether the procedure failed because the incorrect region of tissue was ablated, because the ablative tip was not actuated for a sufficient period of time to destroy the target tissue, because the ablative tip was not touching or insufficiently touching the tissue, because the power of the ablative energy was insufficient, or some combination of the above. Upon repeating the ablation procedure so as to again attempt to ablate the target tissue, the clinician may have as little feedback as during the first procedure, and thus potentially may again fail to destroy the aberrant pathway. Additionally, there may be some risk that the clinician would re-treat a previously ablated region of the target tissue and not only ablate the target tissue, but damage adjacent tissues.

In some circumstances, to avoid having to repeat the ablation procedure as such, the clinician may ablate a series of regions of the target tissue along which the target tissue is believed to lie, so as to improve the chance of successful ablation. However, there is again insufficient feedback to assist the clinician in determining whether any of those ablated regions are sufficiently destroyed.

U.S. Pat. No. 4,190,053 to Sterzer describes a hyperthermia treatment apparatus in which a microwave source is used to deposit energy in living tissue to effect hyperthermia. The apparatus includes a radiometer for measuring temperature at depth within the tissue, and includes a controller that feeds back a control signal from the radiometer, corresponding to the measured temperature, to control the application of energy from the microwave source.

U.S. Pat. No. 7,769,469 to Carr et al. describes an integrated heating and sensing catheter apparatus for treating arrhythmias, tumors and like, having a diplexer that permits near simultaneous heating and temperature measurement. This patent too describes that temperature measured by the radiometer may be used to control the application of energy, e.g., to maintain a selected heating profile.

Despite the promise of precise temperature measurement sensitivity and control offered by the use of radiometry, there have been few successful commercial medical applications of this technology. One drawback of previously-known systems has been an inability to obtain highly reproducible results due to slight variations in the construction of the microwave antenna used in the radiometer, which can lead to significant differences in measured temperature from one catheter to another. Problems also have arisen with respect to orienting the radiometer antenna on the catheter to adequately capture the radiant energy emitted by the tissue, and with respect to shielding high frequency microwave components in the surgical environment so as to prevent interference between the radiometer components and other devices in the surgical field.

Acceptance of microwave-based hyperthermia treatments and temperature measurement techniques also has been impeded by the capital costs associated with implementing radiometric temperature control schemes. Radiofrequency ablation techniques have developed a substantial following in the medical community, even though such systems can have severe limitations, such as the inability to accurately measure tissue temperature at depth, e.g., where irrigation is employed. However, the widespread acceptance of RF ablation systems, extensive knowledge base of the medical community with such systems, and the significant cost required to changeover to, and train for, newer technologies has dramatically retarded the widespread adoption of radiometry.

U.S. Pat. Nos. 8,926,605 and 8,932,284 to McCarthy et al., the entire contents of each of which are incorporated herein by reference, describe systems for radiometrically measuring temperature during ablation.

In view of the foregoing, it would be desirable to provide systems and methods that permit a high degree of radiometric measurement of temperature at depth in tissue to achieve accurate temperature measurement with microwave heating.

It would further be desirable to provide systems and methods for calibration of such microwave heating and radiometric measurement systems.

In addition, it would be desirable to provide an ablation system having feedback mechanisms for detecting and/or preventing overheating of target tissue during an ablation procedure to improve efficacy and safety of the ablation system.

While there is a breadth of energy based devices to treat a range of conditions, giving promise of improved outcomes, lower risks and shortened recovery times, there remains significant opportunity to exploit capabilities of distinct technologies to deliver optimal therapy to drive outcome and improve risk profiles.

SUMMARY OF THE INVENTION

The present invention provides ablation systems and methods for ablating target tissue as well as sensing parameters (e.g., temperature) during ablation. In a preferred embodiment, the ablation systems utilize microwave energy for ablation. For example, the system for ablating target tissue within a patient may include a catheter having a proximal region and a distal region, and a main antenna disposed at the distal region of the catheter. The main antenna may both emit energy to ablate the target tissue and measure a radiometer temperature generated as a result of the energy emission. The system further includes a reference termination disposed at the distal region of the catheter for measuring a reference temperature at the distal region. The system is designed for safe and efficacious energy delivery into tissue by, for example, emitting energy in a controlled, repeatable manner that allows for feedback and energy emission titration based on sensed parameters (e.g., tissue temperature) measured during ablation. The system may include a cooling sleeve disposed over at least the distal region of the catheter. The cooling sleeve may be coupled to a source of coolant and to permit the coolant to flow over the main antenna and the reference termination, thereby cooling the main antenna and the reference termination during pre-ablation calibration and during an ablation procedure. In this manner, ex vivo calibration prior to the in vivo ablation procedure closely aligns with the ablation procedure to ensure accurate sensing of parameters such as target tissue during ablation.

Additionally, the system further may include a processor operatively coupled to the main antenna and the reference termination. The processor may cause the main catheter to emit energy and measure radiometer temperature and the reference termination to measure reference temperature in an interleaving manner. For example, processor may cause the main catheter to emit energy for a first time period, and to cause the main catheter to measure radiometer temperature and the reference termination to measure reference temperature in an alternating manner for a second time period. The first time period may be at least 80% of a sum of the first and second time periods. Moreover, the processor may be programmed to cause the main catheter to measure radiometer temperature and the reference termination to measure reference temperature in an alternating manner via a switch electrically coupled to the main antenna and the reference termination.

The processor may be programmed to calculate a target tissue temperature based on the measured radiometer temperature and the measured reference temperature. Moreover, the processor may be programmed to estimate a volume of an ablation lesion created by the energy emission during the ablation procedure based on the target tissue temperature. For example, the ablation lesion volume may be estimated based on at least one of an average target tissue temperature or an area under a plotted curve of the target tissue temperature. Further, the processor further may permit titration of the energy emission based on the volume of the ablation lesion. In addition, the processor may modulate the energy emission such that the calculated target tissue temperature is maintained within a predetermined threshold.

In accordance with another aspect of the present invention, the processor may be programmed to perform a reference termination calibration to account for heating of the reference termination during energy emission via the main antenna and a radiometer calibration to account for heating of an environment adjacent the target tissue during energy emission via the main antenna. In addition, the processor may be programmed to calculate a target tissue temperature based on the measured radiometer temperature and the measured reference temperature while accounting for heating of the reference termination and the environment adjacent the target tissue during energy emission via the main antenna.

For example, the reference termination calibration may include measuring output voltage resulting from energy emission generated by the reference termination for varying levels of energy emitted by the main antenna while the main antenna and reference termination are in a constant temperature bath providing high fluid flow across the main antenna such that a temperature of an environment adjacent the main antenna remains constant, and comparing the measured voltage with the varying levels of energy emission to account for an effect of energy emission on the reference termination during energy emission.

Moreover, the radiometer calibration may include measuring first and second temperatures in response to impingement of the main antenna with first and second noise levels, respectively, while the main antenna and the reference termination are in a constant temperature bath and comparing the first and second temperatures with the first and second noise levels to account for an effect of energy emission on the environment adjacent the target tissue during energy emission. Alternatively, the radiometer calibration may include measuring a first output voltage and a first temperature in response to a first radiometer signal while the main antenna and reference termination are in a first bath having a first temperature, measuring a second output voltage and a second temperature in response to a second radiometer signal while the main antenna and reference termination are in a second bath having a second temperature different from the first temperature, and comparing the first and second output voltages with the first and second temperatures to account for an effect of energy emission on the environment adjacent the target tissue during energy emission.

In accordance with yet another aspect of the present invention, the processor may be programmed to calculate a target tissue temperature based on the measured radiometer temperature and the measured reference temperature, and to monitor the target tissue temperature to predict and/or detect a pop, e.g., a rapid target tissue temperature rise followed by a sudden target tissue temperature drop, within the target tissue temperature. Accordingly, the processor may generate an alert if the pop is detected. Moreover, the processor may be programmed to automatically modulate the energy emission via the main antenna to reduce at least one of the target tissue temperature or a rate of increase of the target tissue temperature if the pop is predicted. In addition, the system further may include a display operatively coupled to the processor, such that the processor causes the display to display the pop within the target tissue temperature.

In accordance with another aspect of the present invention, an alternative system for ablating target tissue within a patient is provided. The system may include a catheter having a proximal region and a distal region, and a main antenna having a monopole. The main antenna may be disposed at the distal region of the catheter and may emit energy to ablate the target tissue and measure a radiometer temperature generated as a result of the energy emission. In addition, the system may include a reference termination disposed at the distal region of the catheter, such that the reference termination may measure a reference temperature at the distal region. Moreover, the system may include a processor operatively coupled to the main antenna and the reference termination, the processor configured to: cause the main catheter to measure radiometer temperature and the reference termination to measure reference temperature in an alternating manner via a switch electrically coupled to the main antenna and the reference termination; and calculate a target tissue temperature based on the measured radiometer temperature and the measured reference temperature.

The monopole may include a proximal radiating element and a distal radiating element, such that a proximal end of the proximal radiating element has a short designed to defeat a choke action of the proximal radiating element. Accordingly, the switch may be disposed between the proximal radiating element and the distal radiating element. Alternatively, the switch may be disposed within a proximal region of the proximal radiating element, wherein the proximal region is proximal to a junction between the proximal radiating element and the distal radiating element.

The switch may include first and second switching diodes. Moreover, the switch further may include a third switching diode which improves isolation of the reference termination from the radiometer temperature during ablation of the target tissue. Additionally, the switch may include a fourth switching diode which improves isolation of the reference termination from the radiometer temperature during measurement of the reference temperature. The second switching diode and the fourth switching diode may be in series with the main antenna, and separated by a microstrip transmission line. The system further may include a switch module sized and shaped to house the switch. The switch module may include proximal and distal coaxial connectors structured to be removeably coupled to a coaxial cable of the catheter.

BRIEF DESCRIPTION OF THE DRAWINGS

FIG. 5A illustrates an exemplary microwave ablation system where the reference termination is disposed between the dipoles of the radiometer antenna, FIG. 5B illustrates the switching network of the microwave ablation system of FIG. 5A.

FIG. 21A-21C illustrate results of heat sink testing using an ablation system in accordance with the principles of the present invention.

FIGS. 27A and 27B illustrate an exemplary microwave ablation system where the switching network is pushed back in accordance with the principles of the present invention.

DETAILED DESCRIPTION OF THE INVENTION

Figure 1:
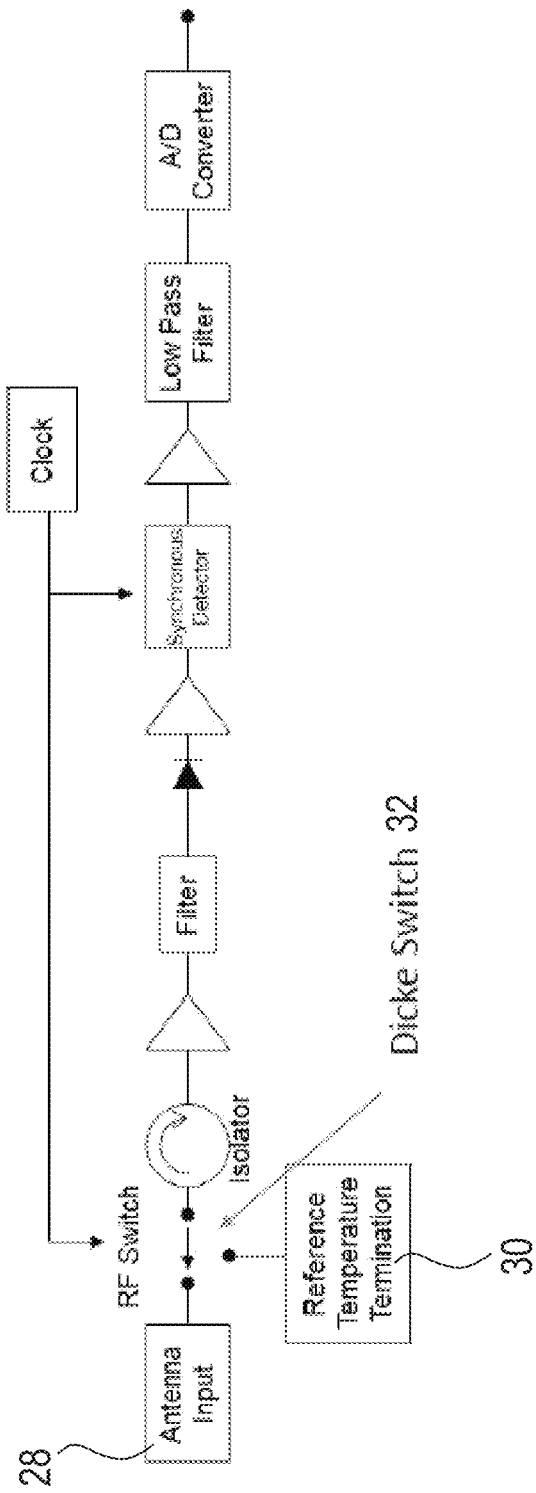
FIG. 1 is a simplified block diagram of a microwave radiometer having a Dicke switch.

In view of the foregoing, it would be desirable to provide systems and methods for treating living tissue that employs a radiometry system, e.g., a microwave radiometry system, for temperature measurement and control. In accordance with one aspect of the invention, systems and methods are provided for radiometrically measuring temperature during microwave ablation, i.e., calculating temperature based on signal(s) from a radiometer. In a microwave ablation system, the antenna determines how the ablation signal power is distributed within the target tissue. This can be quantified as power loss density. In a radiometric sensing system, the antenna works exactly in reverse where power loss density becomes the power source density. The total received power is the sum of all the power sources in the measurement volume. The relative received magnitude of the power sources is the same as the relative dissipation magnitudes of the power losses for the transmitting or ablation case.

Unlike standard thermocouple techniques used in existing commercial ablation systems, a radiometer may provide useful information about tissue temperature at depth—where the tissue ablation occurs—and thus provide feedback to the clinician about the extent of tissue damage as the clinician ablates a selected region of the target tissue. Specifically, the present disclosure overcomes the drawbacks of previously-known systems by providing improved systems and methods for microwave ablation of target tissue, and measuring temperature of the target tissue during ablation. Moreover, the present disclosure provides improved systems and methods for calibrating the ablation system to account for effects of energy emission on the reference termination and the environment adjacent the antenna, estimating ablation lesion volume, and detecting and/or predicting a pop condition indicative of undesirable heating and/or movement of the ablation system, thereby improving safety and efficacy of the system. The novel inventions described herein may have broad application to catheter/probe-based therapies, including but not limited to targets in the vascular system and soft tissue targets in liver, kidney, prostate and lung. For example, the principles of the present invention described herein may be incorporated into known ablation systems such as NeuWave™ Microwave Ablation System (available by Ethicon, part of Johnson & Johnson, Bridgewater, New Jersey and Cincinnati, Ohio).

Microwave heating to target tissue and microwave radiometry as a means of monitoring the temperature of the heated tissue ensures that the desired temperatures are delivered to adequately treat the target tissue and achieve therapeutic goals, and are described in U.S. Patent Application Pub. No. 2019/0365466 to Allison, the entire contents of which are incorporated herein by reference. Specifically, heating and temperature sensing is accomplished with a catheter using a single antenna which is shared for both functions. The microwave heating may be directed toward the target tissue. A radiometer, operating at the same frequency and time sharing the antenna with the microwave generator, senses the microwave emissions from the region surrounding the antenna and converts these to tissue temperature. In this case, the volume of tissue being monitored includes, e.g., tumorous lung tissue. An algorithm relates the temperature at the target region to the volume temperature reading.

However, there are obstacles to achieving accurate temperature measurement using radiometry with microwave heating. These result from the dissipative losses in the relatively long coaxial cable between the radiometer and the antenna. The usual approach uses a Dicke radiometer which compares the unknown temperature of the target tissue being heated to an internal reference of known temperature in the radiometer. The radiometer output voltage is:

$$V_{rad} = (T_{tissue} - T_{reference}) \times \text{Slope} + \text{Offset}$$

Where Slope is the volts per degree sensitivity and Offset is the sum of all the fixed errors. These constants are determined by calibration using a hot and cold input termination.

$$\Delta T = \frac{2 \times (T_{antenna} + \text{radio meter noise temperature})}{\sqrt{BW \times t}}$$

FIG. 1 illustrates a simplified block diagram of such a system having a Dicke radiometer. As shown in FIG. 1, an input switch, e.g., Dicke switch 32, is used that selects either antenna input 28 or an internal reference input, e.g., reference temperature termination 30. The approach is popular because everything in the measurement path behind Dicke switch 32 is common to both the target measurement from antenna input 28 and the reference measurement from reference temperature termination 30, and most of the possible measurement errors drop out of the calculations.

The problem with antenna catheters is the dissipative loss in the coaxial cable running the length of the catheter. The emissions resulting from the cable losses are indistinguishable from the emissions received by the antenna. The radiometer measures the antenna temperature combined with the cable temperature. The problem is aggravated by the desire for small diameter catheters requiring high loss, small diameter coaxial cables, and heating of the coaxial cable caused by dissipation of some of the generator power.

Figure 2:
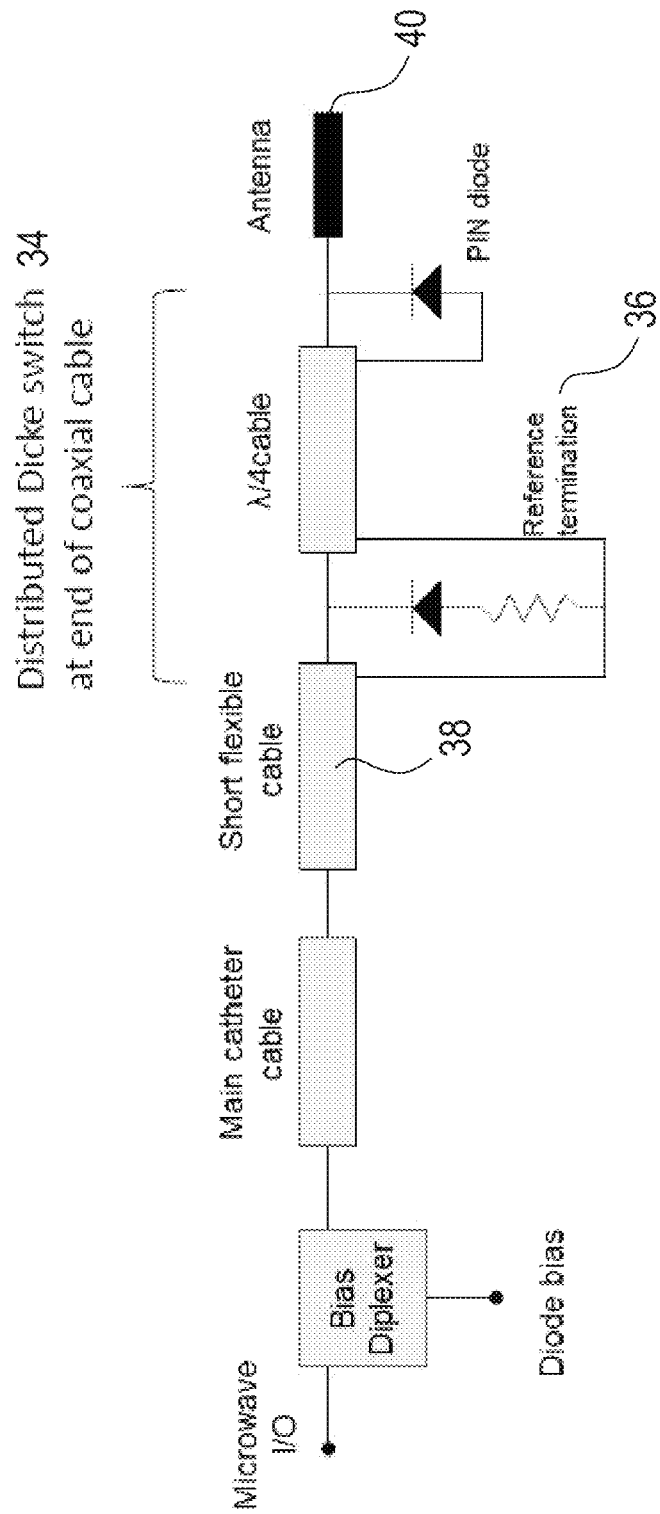
FIG. 2 is a block diagram of a microwave heating and temperature sensing system where the Dicke switch and reference termination are disposed at the end of the coaxial cable near the connection to the antenna.

A solution is disclosed in the block diagram of FIG. 2. As illustrated in FIG. 2, Dicke switch 34 and reference termination 36 have been moved out to the end of the coaxial cable, e.g., short flexible cable 38 at the distal end of the main catheter cable, near the connection to antenna 40. Now the coaxial cable is part of both the target measurement from antenna 40 and the reference measurement from reference termination 36, and heat dissipating therefrom drops out of the temperature calculation. However, the scheme is subject to some error resulting from heating of the reference due to its proximity to the heating cable.

Figure 3:
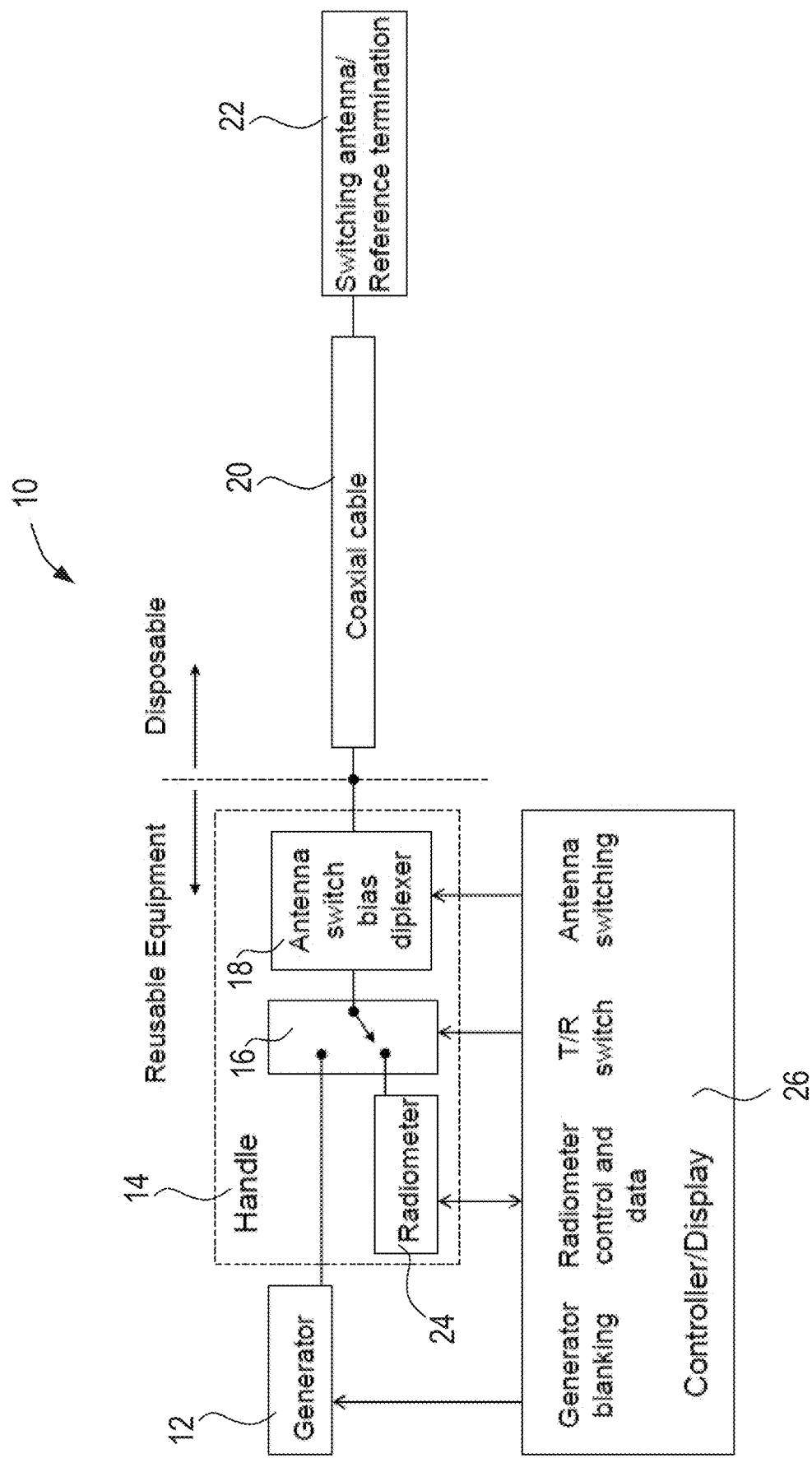
FIG. 3 is a block diagram of an exemplary microwave ablation system constructed in accordance with the principles of the present invention.

To overcome the drawbacks of previously-known radiometry systems, the present invention integrates the Dicke switch radiometer function integrated into the antenna. For example, referring now to FIG. 3, a block diagram illustrating microwave heating and temperature sensing system 10 constructed in accordance with the principles of the present invention is provided. As shown in FIG. 3, generator 12 supplies ablative energy to switching antenna 22 through Transmit/Receive (T/R) switch 16 followed by antenna switch bias diplexer 18. Generator 12 may be any previously-known commercially available ablation energy generator, e.g., a microwave energy generator, thereby enabling radiometric techniques to be employed with reduced capital outlay.

Further, radiometer 24 receives temperature measurements from switching antenna 22 via cable 20, e.g., coaxial cable. Switching antenna 22 includes a main antenna having one or more microwave radiating elements for emitting microwave energy and for measuring temperature of tissue adjacent the main antenna, and a reference termination for measuring a reference temperature. In addition, switching antenna 22 includes a switching network, e.g., a Dicke switch, integrated therein for detecting the volumetric temperature of tissue subjected to ablation. The switching network selects between the signals indicative of measured radiometer temperature from the main antenna of switching antenna 22, e.g., the temperature of the tissue adjacent the main antenna during the ablation procedure, and signals indicative of the measured reference temperature from the reference termination of switching antenna 22. As the switching network is integrated within switching antenna 22, and sufficiently far from the connection point of cable 20 and switching antenna 22, heating of the reference termination by cable 20 is avoided.

Switch 16 and antenna switch bias diplexer 18 may be disposed within handle 14, along with radiometer 24 for receiving temperature measurements from switching antenna 22 depending the state of switch 16. For example, switch 16 may be in an ablation state such that microwave power may be transmitted from generator 12 to switching antenna 22, or switch 16 may be in a measurement state such that radiometer 24 may receive temperature measurement from switching antenna 22, e.g., from the main antenna and/or the reference termination. Accordingly, switch bias diplexer 18 may be in a main antenna state such that radiometer 24 may receive temperature measurement from the main antenna, or switch bias diplexer 18 may be in a reference termination state such that radiometer 24 may receive temperature measurement from the reference termination. Handle 14 may be reusable, while cable 20 and switching antenna 22 may be disposable.

System 10 further includes controller 26 coupled to generator 12 and switching antenna 22 via, e.g., handle 14 and cable 20, to coordinate signals therebetween. Controller 26 thereby provides generator 12 with the information required for operation, transmits ablative energy to switching antenna 22 under the control of the clinician, and may display via a temperature display the temperature at depth of tissue as it is being ablated, for use by the clinician. The displayed temperature may be calculated based on signal(s) measured by switching antenna 22 using computer algorithms. Thus, controller 26 includes a processor having memory for storing instructions to be executed by controller 26. The processor may comprise one or more commercially available microcontroller units that may include a programmable microprocessor, volatile memory, nonvolatile memory such as EEPROM for storing programming, and nonvolatile storage, e.g., Flash memory, for storing firmware. The memory of the processor stores program instructions that, when executed by the processor, cause the processor and the functional components of system 10 to provide the functionality ascribed to them herein. The processor is configured to be programmable such that programming data is stored in the memory of the processor or accessible via a network. As will be readily understood to one skilled in the art, while FIG. 3 is illustrated to show one controller, the processor may include multiple processors utilized in a single location/housing or multiple locations/housings. Further, the reusable equipment in FIG. 3 may be housed in a common housing or separate housings.

The processor may direct switch 16 to move between the ablation state and the measurement state as described above. For example, the processor may cause the main antenna of switching antenna 22 to emit microwave energy when switch 16 is in the ablation state, and may cause the radiometer 24 to receive signals indicative of temperature measurement from switching antenna 22, e.g., from the main antenna and/or the reference termination, when switch 16 is in the measurement state. In addition, the processor may direct switch bias diplexer 18 to move between the main antenna state and the reference termination state as described above. For example, the processor may receive signals indicative of measured radiometer temperature from the main antenna of switching antenna 22, e.g., the temperature of the tissue adjacent switching antenna 22 during the ablation procedure, when switch bias diplexer 18 is in the main antenna state, and signals indicative of the measured reference temperature from the reference termination of switching antenna 22 when switch bias diplexer 18 is in the reference termination state. Accordingly, the processor can calculate the volumetric temperature of the tissue subject to ablation based on the signals. Moreover, the processor may modulate the level of energy emitted via main antenna 43 based on the calculated volumetric temperature of the tissue subject to ablation continuously as part of a feedback loop to ensure that the temperature of the target tissue is maintained within a predetermined threshold.

In accordance with one aspect of the present invention, the processor directs switch 16 to be positioned in the ablation state for a majority of an ablation period, e.g., more than 50%, more than 75%, more than 80%, or preferably more than 90%, to maximize the power dissipated. Accordingly, the processor may direct switch 16 to be positioned in the measurement state for the remainder of the ablation period, e.g., less than 50%, less than 25%, less than 20%, or preferably less than 10%, respectively. Moreover, during the ablation period when switch 16 is in the measurement state, the processor may direct switch bias diplexer 18 to alternate between being positioned in the main antenna state and the reference termination state.

For example, in a one second cycle, the processor may direct switch 16 to be positioned in the ablation state for 900 milliseconds such that the main antenna emits microwave energy to the target tissue for 900 milliseconds, and then direct switch 16 to be positioned in the measurement state for 100 milliseconds. During the 100 milliseconds that switch 16 is in the measurement state, the processor may direct switch bias diplexer 18 to alternate between the main antenna state and the reference termination state every, e.g., 1, 2, 3, 4, or 5 milliseconds. As will be understood by a person having ordinary skill in the art, the processor may direct switch 16 to be positioned in the ablation state for more or less than 900 milliseconds, and the processor may direct switch bias diplexer 18 to alternate every time period that include any time less than 1 millisecond or more than 5 milliseconds. Moreover, at least one of the switching components, e.g., switch 16 and switch bias diplexer 18, may be integrated in switching antenna 22 as described in further detail below.

The microwave power propagates from generator 12 down cable 20 in the catheter to switching antenna 22 at the catheter tip. The microwave power radiates outward from the main antenna of switching antenna 22 into the target tissue (e.g., target lung tissue such as a tumor). In other examples, such as where the ablation system is used for denervation, an introducer device may be used to deliver the catheter within the body lumen, and a spacer device may be used to ensure that switching antenna 22 is deployed in the approximate center of the body lumen. The volume of blood flowing through the body lumen at body temperature may cool the surface of the body lumen in immediate contact with the blood. In addition to, or alternatively, coolant from outside the body, introduced through a coolant lumen of the catheter may be used to cool the surface of the surface of the body lumen. Tissue beyond the lumen wall, that does not experience this cooling, heats up. Sufficient microwave power is supplied to heat the target tissue (e.g., nerve area) to a temperature that destroys the target tissue.

Figure 4B:
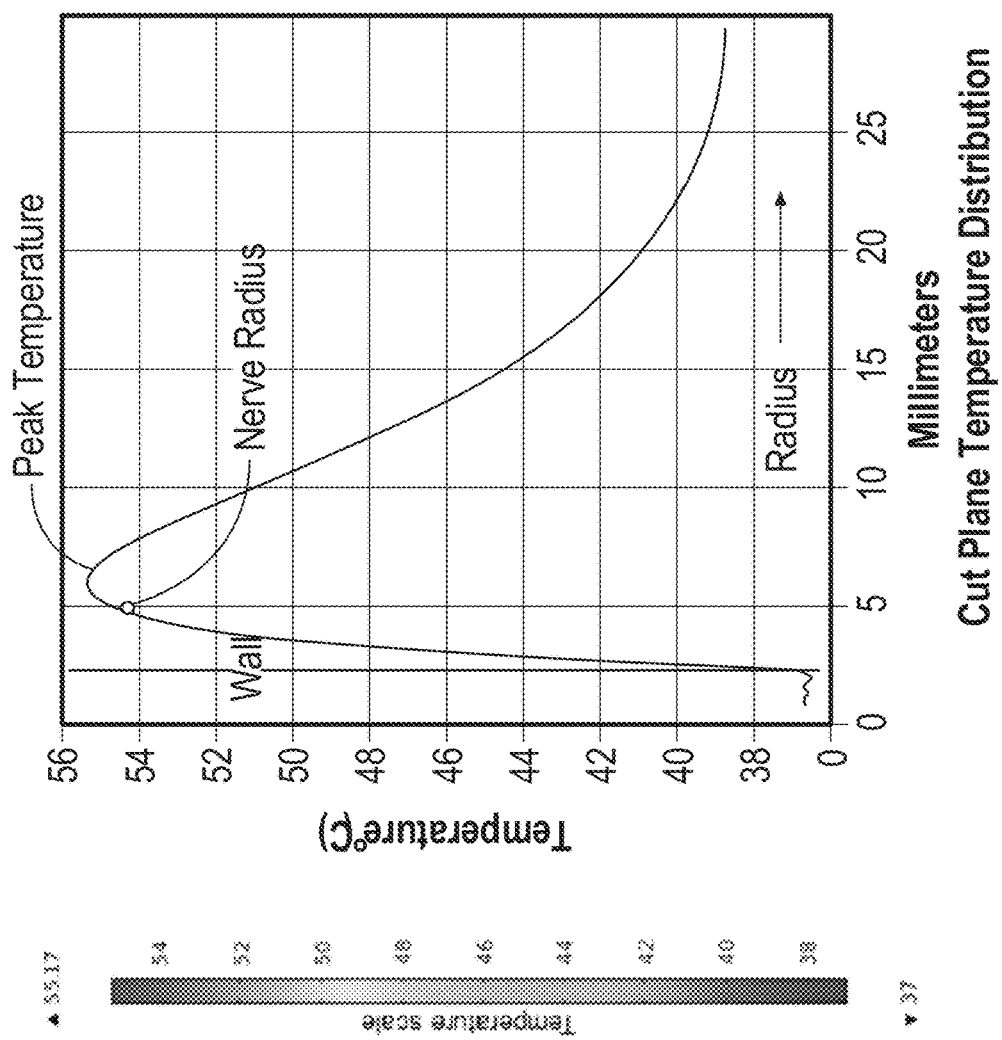
FIG. 4B illustrates the cut plane temperature distribution.
Figure 4A:
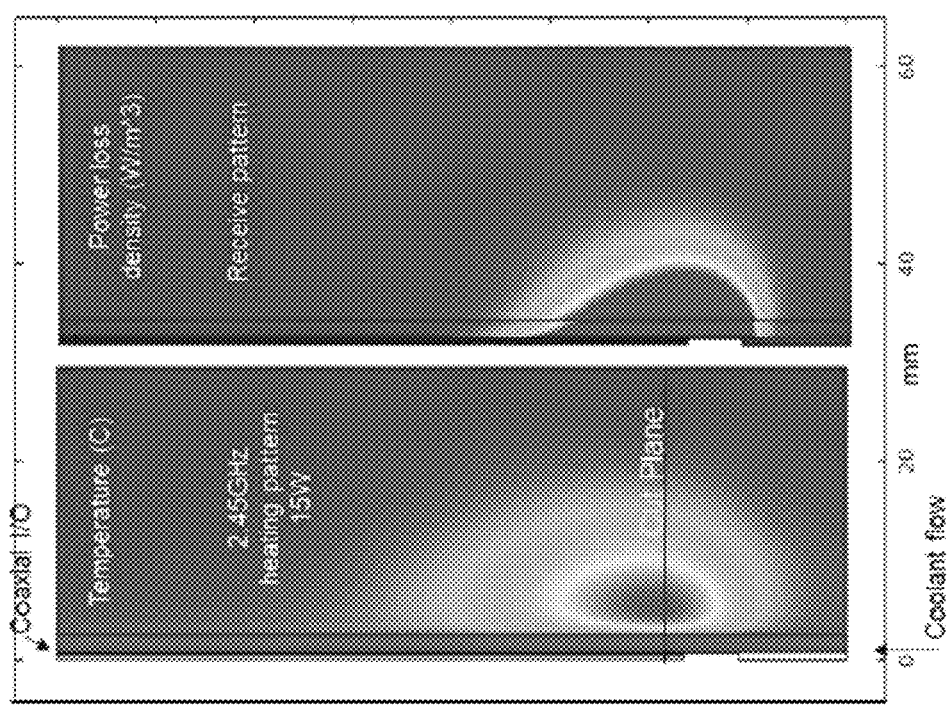
FIG. 4A illustrates a computer simulation of the temperature field and power loss density created by the microwave heating of the system of FIG. 3.

A computer simulation of the temperature field created by microwave heating is shown in FIG. 4. FIG. 4 illustrates a cut through the switching antenna and surrounding tissue. The effect is symmetrical around the antenna so just one half of the cut plane is shown. The temperature along a radial line through the peak temperature shows the temperature within the target tissue. The temperature rises inside the tissue near the tissue surface and reaches a maximum at a depth near the target tissue. FIG. 4 also illustrates the microwave power loss density pattern perceived by the switching antenna. Since the switching antenna and frequency are common to both the generator and radiometer, the patterns produced for both functions are coincident and the radiometer optimally monitors the heated region.

Figure 5C:
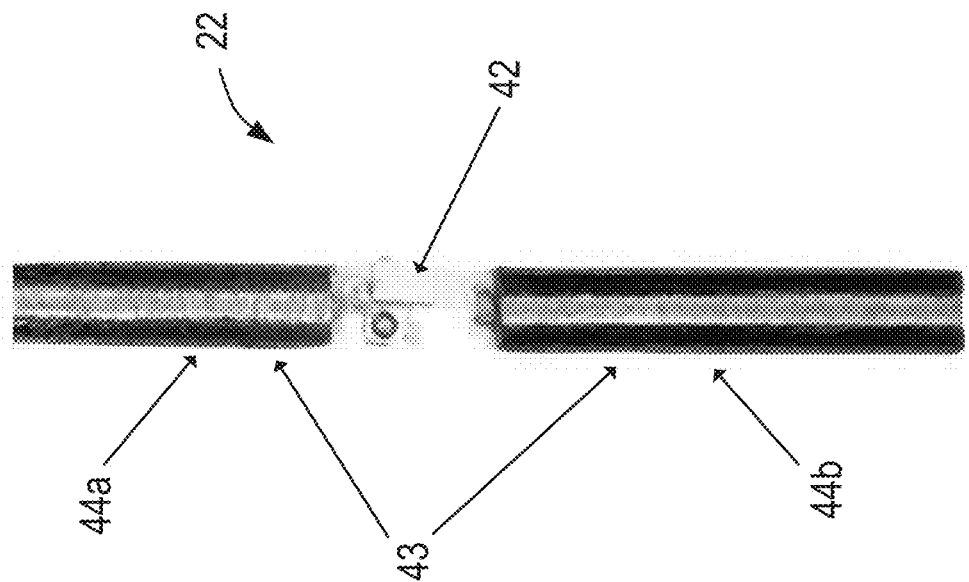
FIG. 5C illustrates the microwave ablation system of FIG. 5A.

Referring now to FIGS. 5A-5C, switching antenna 22 of microwave ablation system 10 is provided. Switching antenna 22 includes main antenna 43 that is used for both microwave heating and temperature sensing, and reference termination 48 for measuring a reference temperature, e.g., temperature adjacent switching antenna 22. For example, main antenna 43 of switching antenna 22 includes one or more microwave radiating elements, e.g., first microwave radiating element 44a and second microwave radiating element 44b, that are designed to receive power from generator 12 via cable 20, and to emit microwave energy into the surrounding target tissue at a level sufficient to ablate the target tissue.

Main antenna 43 of switching antenna 22 further includes means for detecting microwave emissions from the region surrounding the antenna, e.g., one or more circuits formed by microwave radiating elements 44a, 44b, and converts these to temperature of the tissue adjacent switching antenna 22, i.e., radiometer temperature. Switching antenna 22 further includes reference termination 48 for measuring a reference temperature. In addition, switching antenna 22 integrates switching network 42, e.g., a Dicke switch, disposed between the dipole halves of microwave radiating elements 44a, 44b of main antenna 43 of switching antenna 22. As described in detail above, the processor may direct switching network 42 to alternate between permitting microwave energy emission via main antenna 43 and permitting temperature measurement via main antenna 43 or reference termination 48.

The volume temperature output will be the difference between the radiometer temperature, e.g., the temperature of the tissue heated surrounding main antenna 43, and the reference temperature measured by reference termination 48. The volume temperature output may be calculated based on signals indicative of the measured radiometer temperature from microwave radiating elements 44a, 44b of main antenna 43 and the signals indicative of the measured reference temperature from reference termination 48 using algorithms, such as those described in U.S. Pat. Nos. 8,932,284 and 8,926,605, both of which are incorporated herein by reference.

Specifically, all of the switching components, e.g., switching diodes 46a, 46b, and reference termination 48 are located at the junction of the two antenna dipole halves. The junction between the two antenna dipole halves may have a length of, e.g., no more than 5 mm, and preferably no more than 3 mm. Accordingly, the integrated antenna/switch configuration of microwave ablation system 10 is physically shorter and more flexible. Switching diodes 46a, 46b are actuated by biasing switching diodes 46a, 46b ON or OFF, and are switched to the same state in unison. Accordingly, only a single bias source is required and may be operatively coupled to switching diodes 46a, 46b via conductors of cable 20. Switching diodes 46a, 46b may be, e.g., microwave PIN diodes, and are biased with a small forward current in the ON state or back biased with a negative voltage in the OFF state.

In addition, microwave choke arrangement 52 is provided to minimize fold back of the radiating pattern of microwave energy from microwave radiating elements 44a, 44b onto the coaxial catheter shaft. The choke is formed by connecting the proximal dipole half, e.g., microwave radiating element 44a, to cable 20 at the feed point of main antenna 43. A coaxial structure is formed between microwave radiating element 44a and cable 20 which results in the open circuit choke between main antenna 43 and cable 20.

Input from main antenna 43 or from reference termination 48 is selected by reversing the polarity of the bias current applied to center conductor 39 of cable 20. The series-connected switching diodes 46a, 46b are either a small resistance that passes the microwave signal or a small capacitance blocking the signal depending on the bias polarity. Resistors, e.g., bias components 53, return the bias current through outer conductor 41 of cable 110. A bias current diplexer supplies the bias to the proximal end of the catheter outside the body.

The chip level switching components (diodes, resistors and capacitor) are very small and reside on a ceramic card in the short space between the dipole halves of microwave radiating elements 44a, 44b. Cable 20 and the antenna structures are formed of flexible materials that may navigate through tight passages. The only rigid section may be switching network 42, which is no longer than about 3 mm.

System 10 is suitable for applications such as ablation of lung tissue where reference termination 48 must establish a reference temperature. For this reason, reference termination 48 is located on the proximal side of the antenna structure so that a temperature sensor does not have to cross the feed point of main antenna 43 which may disrupt the antenna radiating pattern. A thermocouple circuit formed by outer conductor 41 and a very thin dissimilar metal wire terminating near the reference resistor of reference termination 48 may be used for this purpose.

Figure 6:
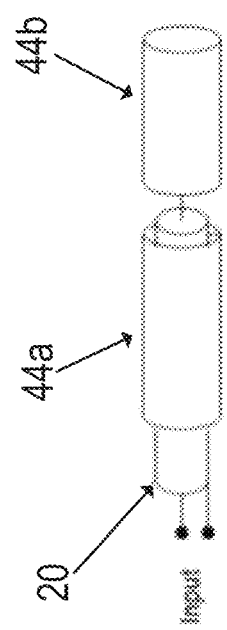
FIG. 6 illustrates a basic dipole of the microwave radiating elements of an exemplary microwave ablation system constructed in accordance with the principles of the present invention.
Figure 7:
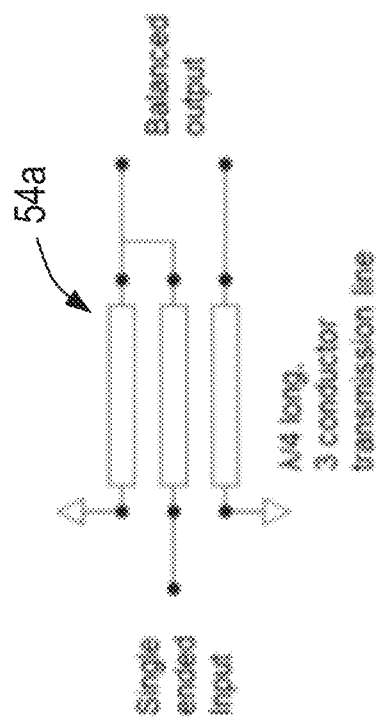
FIG. 7 illustrates a balun transformer of the microwave radiating elements of the exemplary microwave ablation system in accordance with the principles of the present invention.

As illustrated in FIG. 6, microwave radiating elements 44a, 44b are a basic dipole that receives power from generator 12 via cable 20. As shown in FIG. 6, microwave radiating elements 44a, 44b may have a cylindrical shape. As will be understood by a person having ordinary skill in the art, microwave radiating elements 44a, 44b may have other shapes including a spiral winding. Within each of microwave radiating elements 44a, 44b is a balun transformer. The balun transformer transforms a single ended transmission line system to a balance system as shown in FIG. 7, which illustrates balun transformer 54a.

Figure 8:
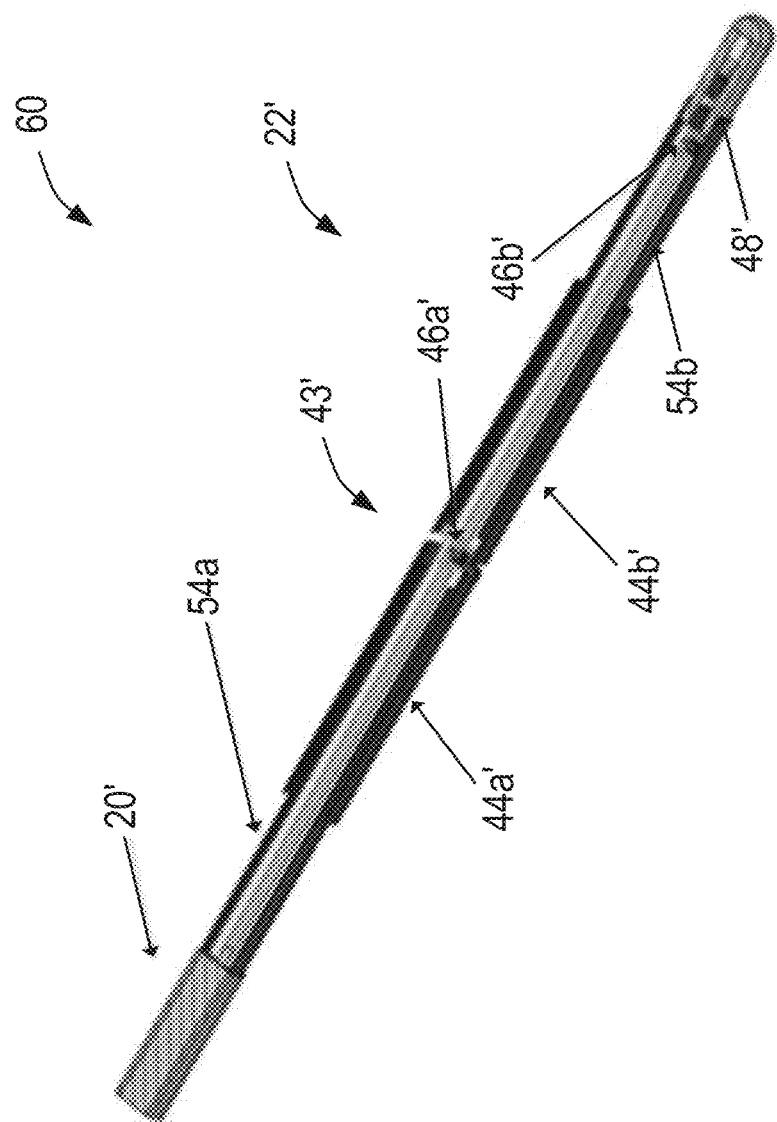
FIG. 8 is a cut away view of a radiometer antenna of the exemplary microwave ablation system constructed in accordance with the principles of the present invention.

Referring now to FIG. 8, alternative exemplary microwave ablation system 60 is provided. Microwave ablation system 60 is constructed similarly to microwave ablation system 10 of FIG. 3 wherein like components are identified by like-primed reference numbers. For example, cable 20' corresponds with cable 20, switching antenna 22' corresponds with switching antenna 22, main antenna 43' corresponds with main antenna 43, microwave radiating elements 44a', 44b' correspond with microwave radiating elements 44a, 44b, switching diodes 46a', 46b' correspond with switching diodes 46a, 46b, and reference termination 48' corresponds with reference termination 48. As shown in FIG. 8, within each of microwave radiating elements 44a, 44b is balun transformer 54a, 54b, respectively.

Microwave ablation system 60 differs from microwave ablation system 10 in that reference termination 48' is disposed distal to second microwave radiating element 44b'. Specifically, switching antenna 22' integrates a switching network, e.g., a Dicke switch including switching diodes 46a', 46b', into main antenna 43' which allows reference termination 48' to protrude out from the distal end of main antenna 43'. Accordingly, system 60 may be used in applications such as renal denervation where reference termination 48' may be maintained at body temperature by blood flow.

The structure of main antenna 43' is unique in that it integrates a radiometer Dicke switch function into a flexible remote antenna and provides for radiometer reference termination 48' to protrude from main antenna 43' into a stable temperature region, e.g., path of blood flow. The volume temperature output will be the difference between the radiometer temperature, e.g., the temperature of the tissue heated surrounding main antenna 43' and the reference temperature, e.g., known stable body temperature provided by blood flow over reference termination 48', e.g., in the renal artery. The volume temperature output may be calculated based on signals indicative of the measured radiometer temperature from microwave radiating elements 44a', 44b' of main antenna 43' and the signals indicative of the measured reference temperature from reference termination 48' using algorithms, such as those described in U.S. Pat. Nos. 8,932,284 and 8,926,605, both of which are incorporated herein by reference.

Figure 9A:
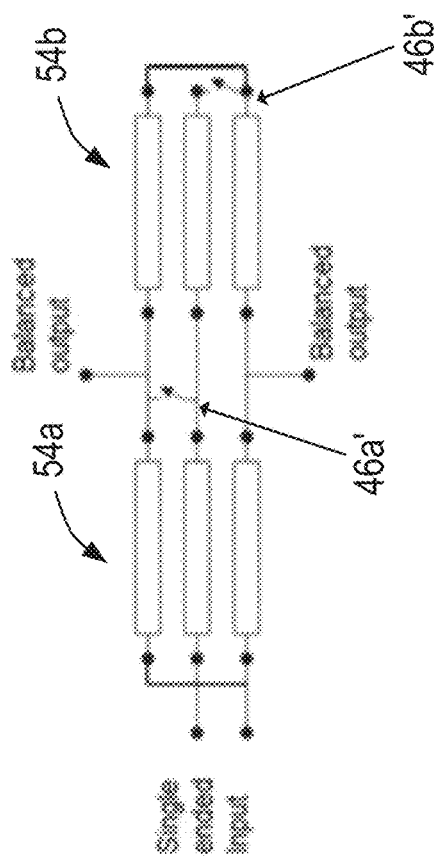
FIG. 9A illustrates back to back balun transformers of the microwave radiating elements of the exemplary microwave ablation system constructed in accordance with the principles of the present invention.
Figure 9B:
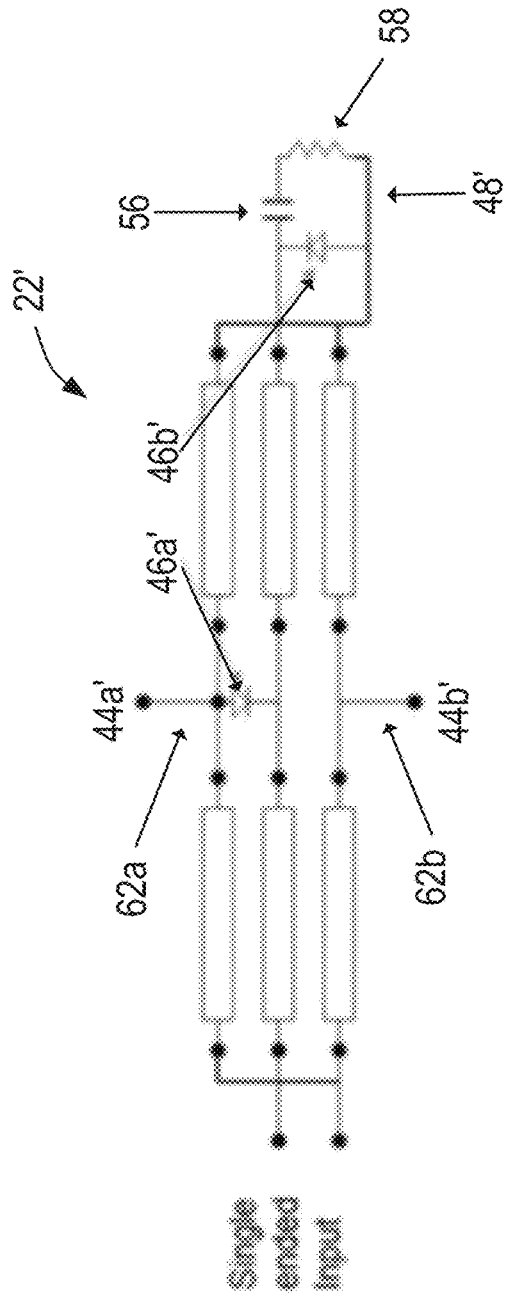
FIG. 9B illustrates the back to back balun transformers of FIG. 9A with switching diodes and a reference termination resistor in accordance with the principles of the present invention.

As illustrated in FIG. 9A, microwave radiating elements 44a', 44b' include two back to back balun transformers 54a, 54b. As shown in FIG. 9B, two switching diodes, e.g., switching diodes 46a', 46b', are integrated within microwave radiating elements 44a', 44b' of main antenna 43'. Switching diode 46a' is positioned between balun transformers 54a, 54b, and switching diode 46b' is positioned distal to balun transformer 54b, e.g., between balun transformer 54b and reference termination 48' (not shown). When switching diodes 46a', 46b' are closed, the single ended input is transformed to the balanced output that connects to microwave radiating elements 44a', 44b'. Balun transformer 54a is shorted at the distal end of main antenna 43', and therefore, transforms to an open circuit at the balanced output. When switching diodes 46a', 46b' are open as shown in FIG. 9A, the transformation is not made and the structure becomes a straight through transmission line path to the distal end of main antenna 43' where the reference termination, e.g., reference termination 48', is located as illustrated in FIG. 9B.

FIG. 9B illustrates switching antenna 22' having back to back balun transformers 54a, 54b, with switching diodes 46a', 46b' integrated therein, and reference termination 48' having bias blocking capacitor 56 and reference termination resistor 58. As further shown in FIG. 9B, connection 62a connects to microwave radiating element 44a', and connection 62b connects to microwave radiating element 44b'. Switching diodes 46a', 46b' are actuated by biasing switching diodes 46a', 46b' ON or OFF, and are switched to the same state in unison. Accordingly, only a single bias source is required and may be operatively coupled to switching diodes 46a', 46b' via conductors of cable 20.

Switching diodes 46a', 46b' may be, e.g., microwave PIN diodes, and are biased with a small forward current in the ON state or back biased with a negative voltage in the OFF state. Bias blocking capacitor 56 prevents bias current from dissipating in reference termination resistor 58 of reference termination 48'. Reference termination resistor 58 may be located any distance from balun transformers 54a, 54b of microwave radiating elements 44a', 44b' to minimize heating of reference termination 48' as long as the connecting transmission line is of the same characteristic impedance as the resistor value of reference termination resistor 58.

Figure 10A:
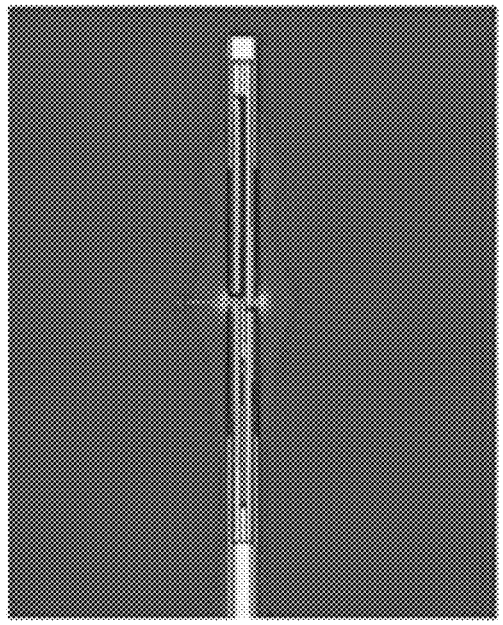
FIG. 10A illustrates the power dissipation in the tissue when the diodes of the exemplary microwave ablation system are biased ON, and FIG. 10B illustrates the power dissipation in the tissue when the diodes of the exemplary microwave ablation system are biased OFF.
Figure 10B:
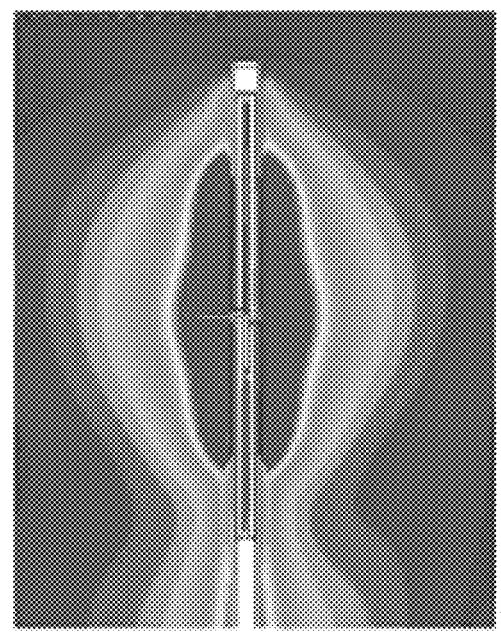

Referring now to FIGS. 10A and 10B, antenna power loss density patterns for both switch positions of switching diodes 46a', 46b', e.g., ON and OFF, is provided. For example, FIG. 10A illustrates power dissipation in the tissue during operation of switching antenna 22' when switching diodes 46a', 46b' are biased ON. As shown in FIG. 10A, a volume of tissue at a predetermined depth within the target tissue, e.g., where the target tissue to be ablated is located, is heated to the desired temperature sufficient for ablation. FIG. 10B illustrates power dissipation in the tissue when switching diodes 46a', 46b' are biased OFF, and thus no dissipation is shown indicating that switching antenna 22' is detecting only reference termination 48'.

Figure 11:
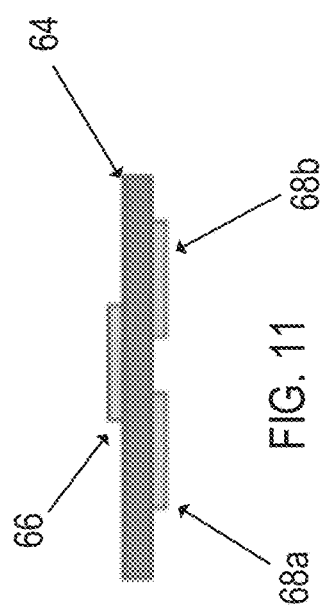
FIG. 11 is a cross-section of a three conductor transmission line of the balun transformer constructed in accordance with the principles of the present invention.

To overcome the challenge of constructing the balun structure and mounting the switching diodes in a flexible, small diameter catheter, a three conductor transmission line structure is used to form balun transformers 54a, 54b as shown in FIG. 11. As illustrated in FIG. 11, thin, flexible dielectric substrate 64 includes center conductor 66 printed on the top surface of substrate 64, and two split ground conductors 68a, 68b printed on the bottom surface of substrate 64. Substrate 64 may be, for example, at most 0.005" thick, and preferably up to 0.005 inches thick. In addition, the dielectric constant of substrate 64 is relatively high, e.g., on the order of at least 10. Transmission line impedance is a function of widths of the conductors and the size of the gap between split ground conductors 68a, 68b.

Figure 12:
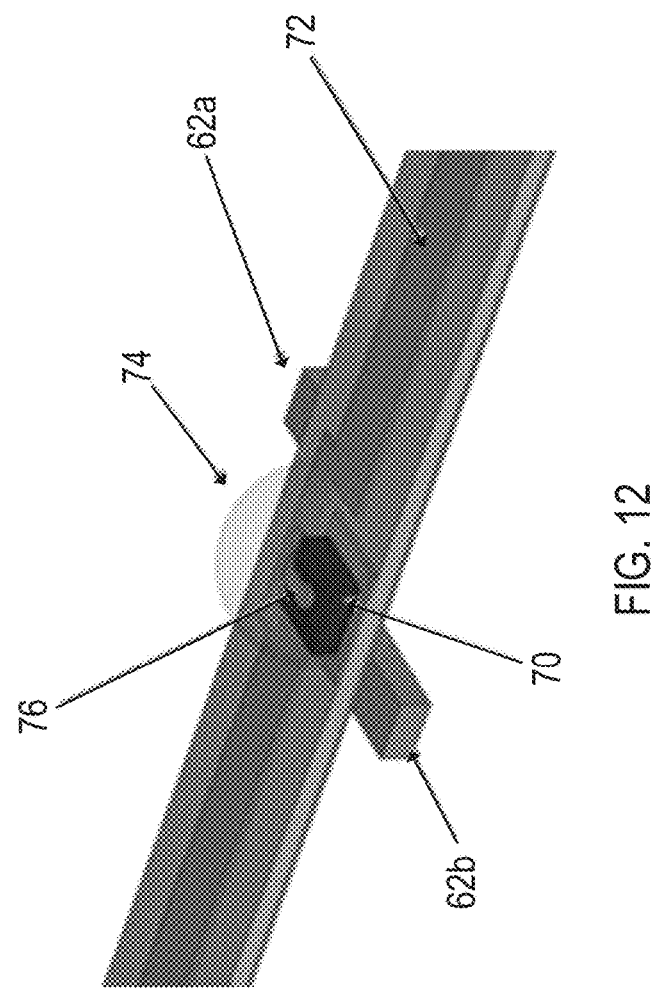
FIG. 12 illustrates encapsulated unpackaged diodes of the exemplary microwave ablation system in accordance with the principles of the present invention.

Switching antenna 22' may need to flex during delivery to the target tissue site, e.g., to make the turn from the femoral artery into the renal artery. To keep the geometry of switching antenna 22' small, unpackaged diodes are used and are encapsulated to prevent damage as main antenna 43' flexes. For example, FIG. 12 illustrates diode chip 70 and ribbon connection 76 positioned on top side circuit trace 72, and encapsulant 74. In addition, FIG. 12 illustrates connection 62a which connects to microwave radiating element 44a', and connection 62b which connects to microwave radiating element 44b'.

In an embodiment where main antenna 43' is stiff in one plane of the substrate, main antenna 43' has flexibility in at least one plane such that it may navigate, e.g., the bends in the arteries of the patient. For example, main antenna 43' may be relatively stiff in the plane of substrate 64 but may curl in the plane perpendicular to substrate 64. This is judged to be adequate flexibility requiring only that the catheter be twisted to orient it with the direction of the required bend. Thus, the structure of main antenna 43' allows main antenna 43' to be flexible in at least one plane, and preferably in both planes. A foam dielectric may be used to fill the regions above and below substrate 64 under microwave radiating elements 44a', 44b'. A braided metal shield layer may also be used to cover balun transformers 54a, 54b under microwave radiating elements 44a', 44b'.

Figure 13:
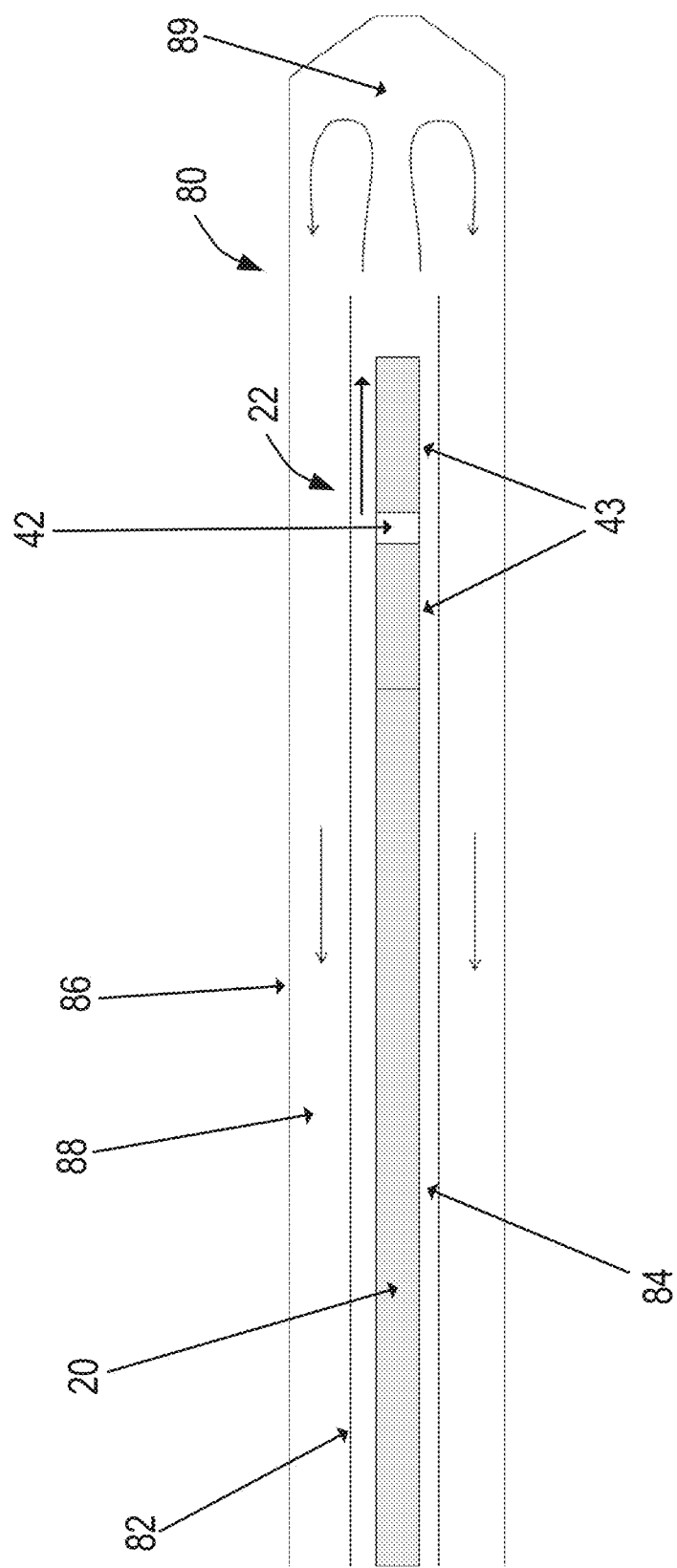
FIG. 13 illustrates an exemplary microwave ablation system having a coolant sleeve constructed in accordance with the principles of the present invention.

Referring now to FIG. 13, an exemplary ablation system having a coolant sleeve disposed thereon is provided. As shown in FIG. 13, coolant sleeve 80 may be disposed over cable 20 and switching antenna 22. Coolant sleeve 80 may include inner tube 82 having passageway 84 sized and shaped to surround cable 20 and switching antenna 22 and to permit a coolant to flow therethrough. Inner tube 82 may be coaxial with cable 20 and switching antenna 22. In addition, coolant sleeve 80 may include outer tube 86 having passageway 88 in fluid communication with passageway 84 of inner tube 82 via junction cavity 89, such that the coolant may flow through passageway 84, junction cavity 89, and out through passageway 88 in the direction of the arrows illustrated in FIG. 13. As shown in FIG. 13, outer tube 86 may also be coaxial with cable 20 and switching antenna 22. Accordingly, the proximal end of coolant sleeve 86 may be fluidly coupled to a source of coolant. As the coolant flows over switching antenna 22, the coolant cools the surface of switching antenna 22 and prevents switching antenna 22 from heating up beyond a predetermined amount. Coolant sleeve 80 may allow for closed-loop cooling such that the coolant is maintained within coolant sleeve 80 and is not expelled into the body of the patient. As described in further detail below, coolant sleeve 86 further may be used to prevent reference termination 42 from heating up beyond a predetermined amount during pre-ablation calibration. The coolant further may be used to cool the surface of the tissue being ablated, thereby allowing for energy to be deposited deeper into the target tissue. Accordingly, peak temperatures are achieved at depth in the tissue rather than at the surface as shown in FIG. 4B.

Figure 14:
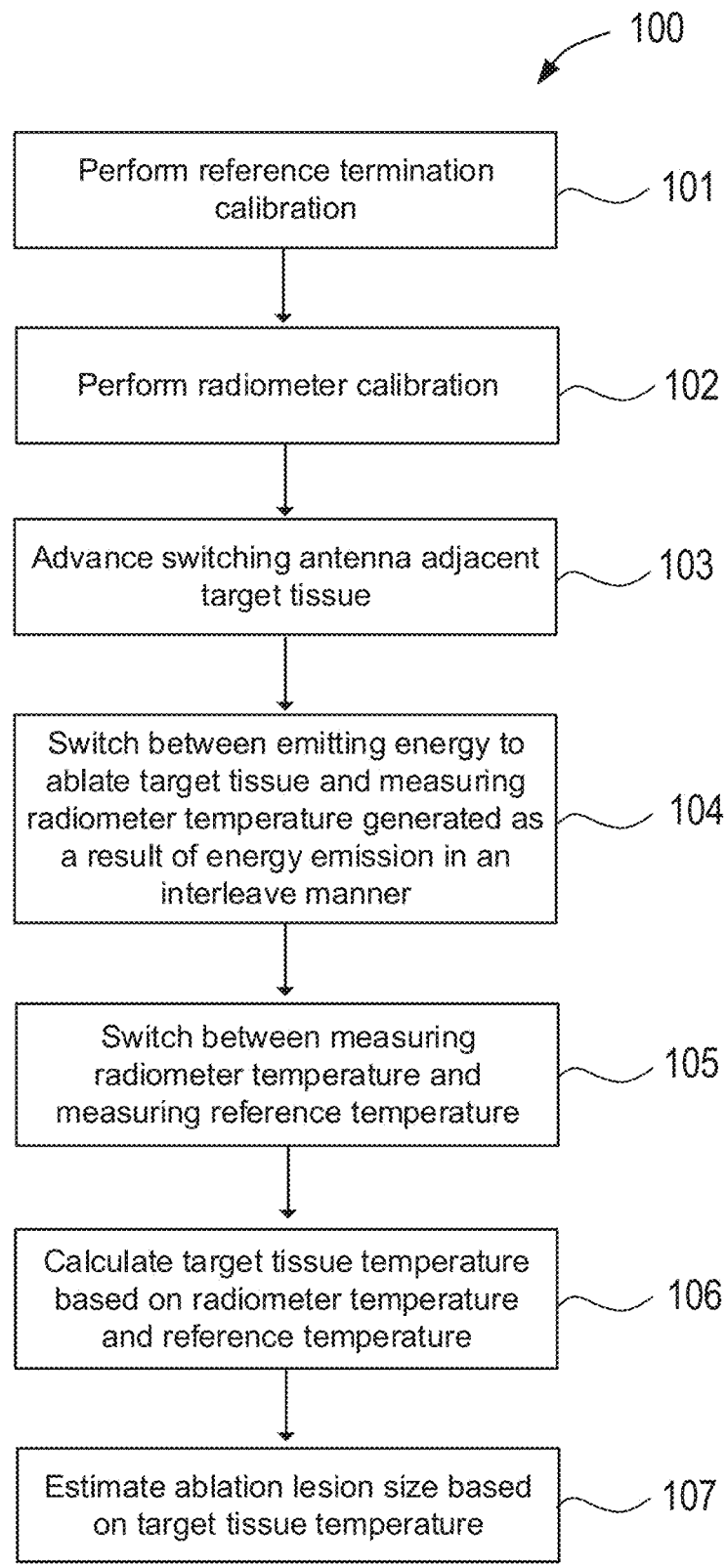
FIG. 14 is a flowchart illustrating the steps ablating target tissue in accordance with the principles of the present invention.

Referring now to FIG. 14, exemplary method 100 for ablating target tissue in accordance with the principles of the present invention is provided. During pre-ablation, at step 101, the processor of the system may perform a reference termination calibration to account for the effect of microwave energy emission on the reference termination. For example, there is a temperature offset between main antenna 43, e.g., the reference temperature sensor (thermocouple) on the outside of switching antenna 22, and reference termination 42, e.g., the microwave reference termination within switching antenna 22. The offset is a function of thermal resistance between main antenna 43 and reference termination 42. Heating of reference termination 42 is caused by dissipation of a small amount of the applied microwave ablation power in main antenna 43. Calibration of reference termination 42 involves using radiometer 24 to measure the temperature rise of reference termination 42 while holding the tissue adjacent switching antenna 22 being measured at a constant temperature.

Figure 15:
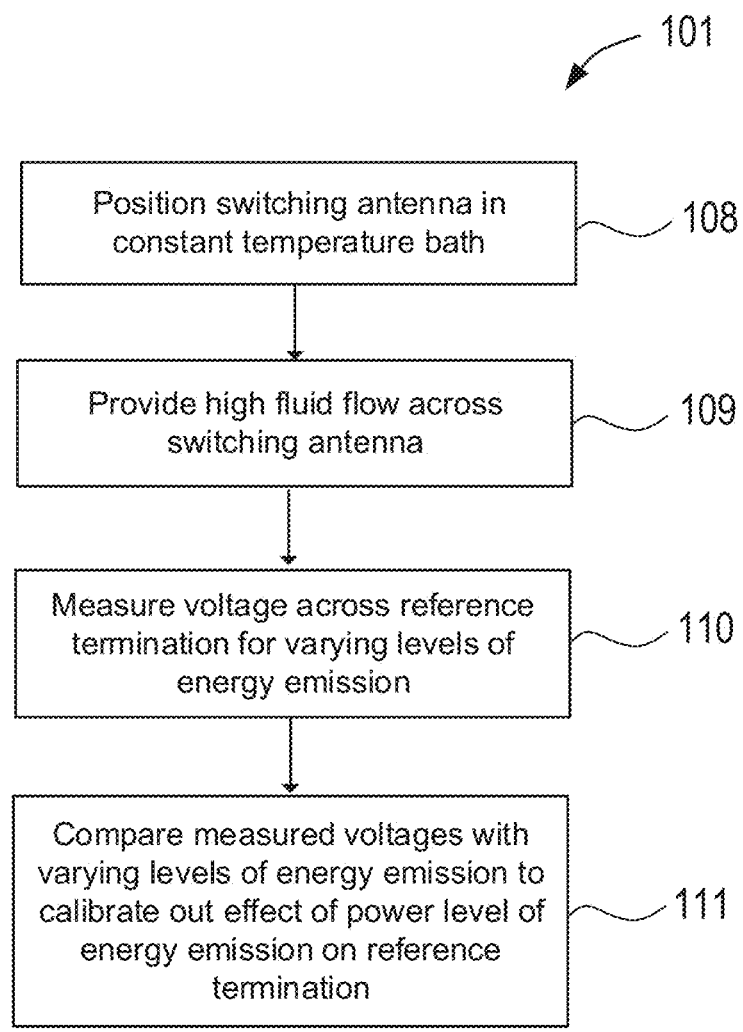
FIG. 15 is a flowchart illustrating the steps of an exemplary reference termination calibration in accordance with the principles of the present invention.

FIG. 15 illustrates exemplary method step 101 for performing a reference termination calibration. At step 108, switching antenna 22 is positioned in a constant temperature bath, which acts as the dissipating tissue. In effect, the normal temperature measurement is conducted backwards where the known reference is the water bath seen by main antenna 43 and the unknown reference is reference termination 42. At step 109, a high, circulating fluid flow may be provided in the bath such that the environment around switching antenna 22 does not heat as the high fluid flow removes all heat generated by the microwave energy emitted from main antenna 43. At step 110, varying levels of microwave energy are emitted via main antenna 22, which causes reference termination 42 to heat slightly due to the microwave energy going through the cable/circuit, and voltage resulting from energy emission generated by reference termination 42 is measured for each of the varying levels of energy emission. As described above, the environment around switching antenna 22 does not heat as the varying levels of microwave energy are emitted due to the high flow bath across main antenna 43. At step 111, the measured voltages are compared with the varying levels of energy emission to account for the effect of energy emission on reference termination 42 during energy emission via main antenna 43. Specifically, comparison of the temperature of reference termination 42 relative to the external temperature sensor reveals a linear relationship with applied microwave power whose slope is the thermal resistance. This thermal resistance constant is multiplied by the applied power level to find the temperature of reference termination 42 during ablations.

Referring again to FIG. 14, during pre-ablation, at step 102, the processor of the system may perform a radiometer calibration to account for the effect of microwave energy emission on the environment adjacent the target tissue during energy emission via main antenna 43. Radiometer calibration provides the ability to determine the sensed microwave energy by radiometer 42 versus the temperature of the environment adjacent the target tissue during energy emission.

Figure 16A:
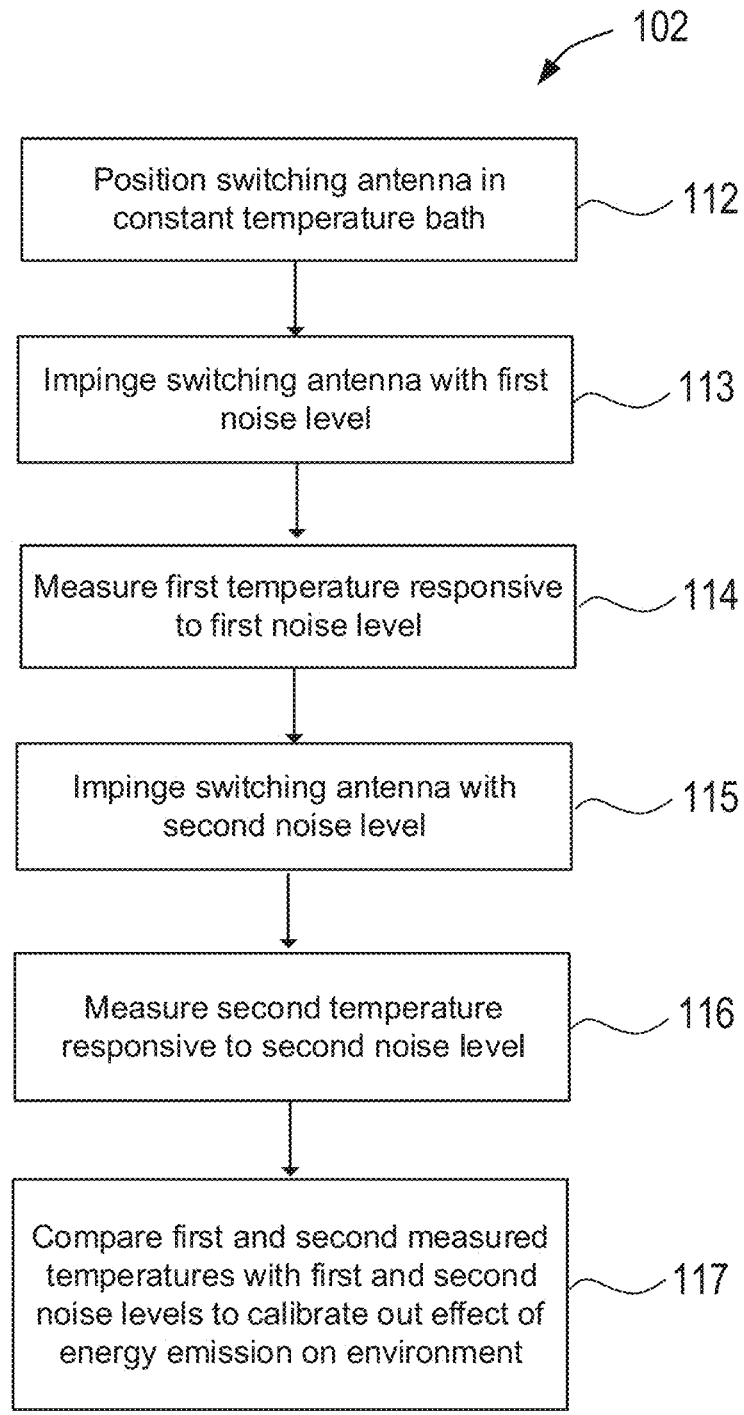
FIG. 16A is a flowchart illustrating the steps of an exemplary radiometer calibration in accordance with the principles of the present invention.

Referring now to FIG. 16A, exemplary method 102 for performing a reference termination calibration is provided. At step 112, switching antenna 22 is positioned in a constant temperature bath. At step 113, using a known microwave noise source that is already calibrated to temperature, main antenna 43 is impinged with a first noise level to create a first known temperature, and at step 114, the first temperature is measured. At step 115, using the known microwave noise source that is already calibrated to temperature, main antenna 43 is impinged with a second noise level different from the first noise level to create a second known temperature, and at step 116, the second temperature is measured. Accordingly, during this radiometer calibration, reference termination 42 need not be cooled. At step 117, the first and second measured temperatures are compared with the first and second noise levels to calibrate out the effect of energy emission via main antenna 43 on the environment adjacent switching antenna 22. Moreover, first and second output voltages resulting from energy emission generated by reference termination 42 may be recorded while measuring the first and second temperatures such that the temperature difference between the first and second temperatures divided by the voltage difference provides the degrees per volt sensitivity of radiometer 24.

Figure 16B:
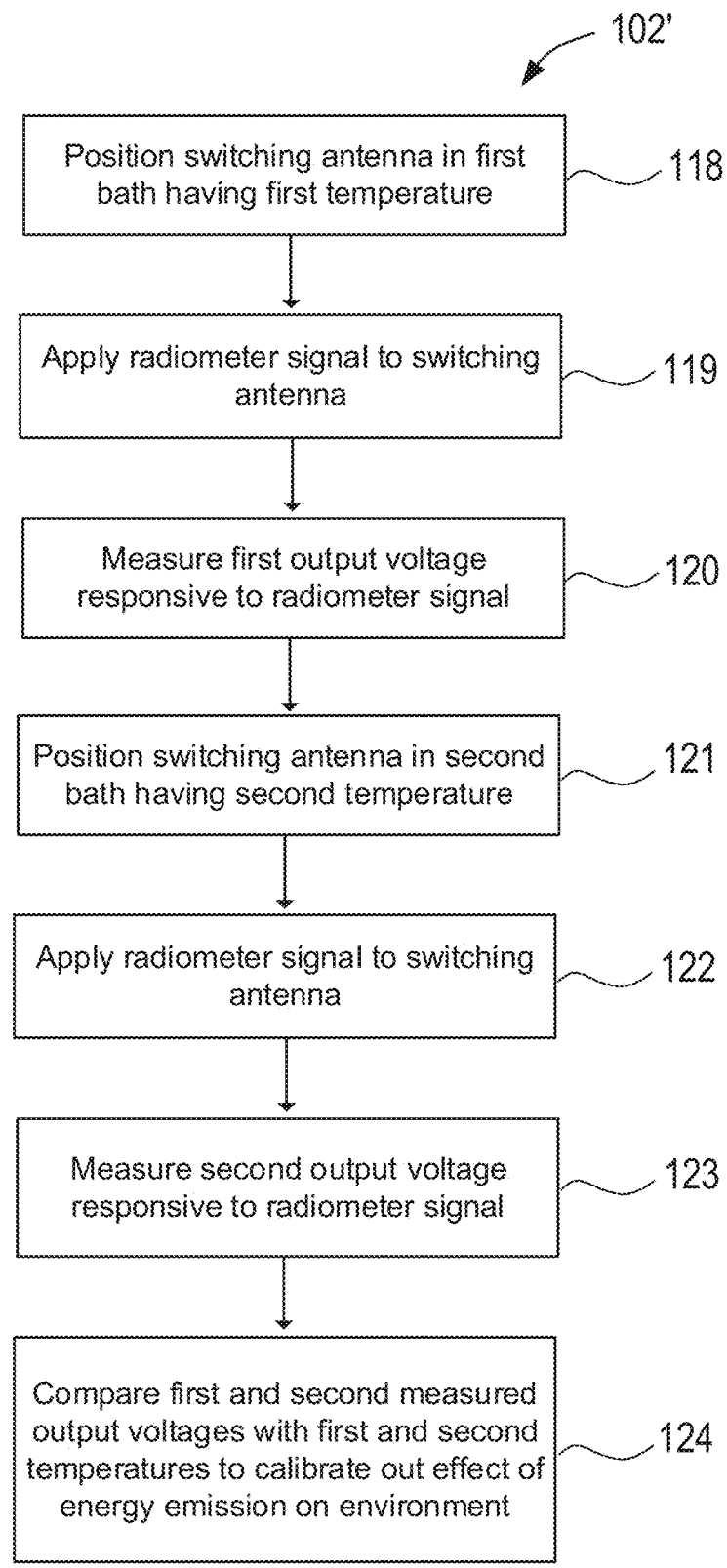
FIG. 16B is a flowchart illustrating the steps of an alternative exemplary radiometer calibration in accordance with the principles of the present invention.

Referring now to FIG. 16B, alternative exemplary method 102' for performing a reference termination calibration is provided. At step 118, switching antenna 22 is positioned in a first bath having a first known temperature. At step 119, a radiometer signal is applied to main antenna 43, and at step 120, a first output voltage resulting from energy emission generated by reference termination 42 responsive to the application of the radiometer signal is measured. At step 121, switching antenna 22 is positioned in a second bath having a second known temperature different from the first temperature. At step 122, the radiometer signal is again applied to main antenna 43, and at step 123, a first output voltage resulting from energy emission generated by reference termination 42 responsive to the application of the radiometer signal is measured. As described above, a coolant may be permitted to flow across switching antenna 22, thereby cooling switching antenna 22. Accordingly, the temperature of reference termination 42 does not change when placed in the two different baths having different temperatures, and the only rise in temperature is that of the unknown environment adjacent switching antenna 22. At step 124, the first and second measure output voltages are compared with the first and second known temperatures to calibrate out the effect of energy emission via main antenna 43 on the environment adjacent switching antenna 22. As will be understood by a person having ordinary skill in the art, a user may use radiometer calibration method 102 or 102', and further may perform reference termination calibration step 101 and radiometer calibration method 102, 102' in any preferred order.

Figure 17:
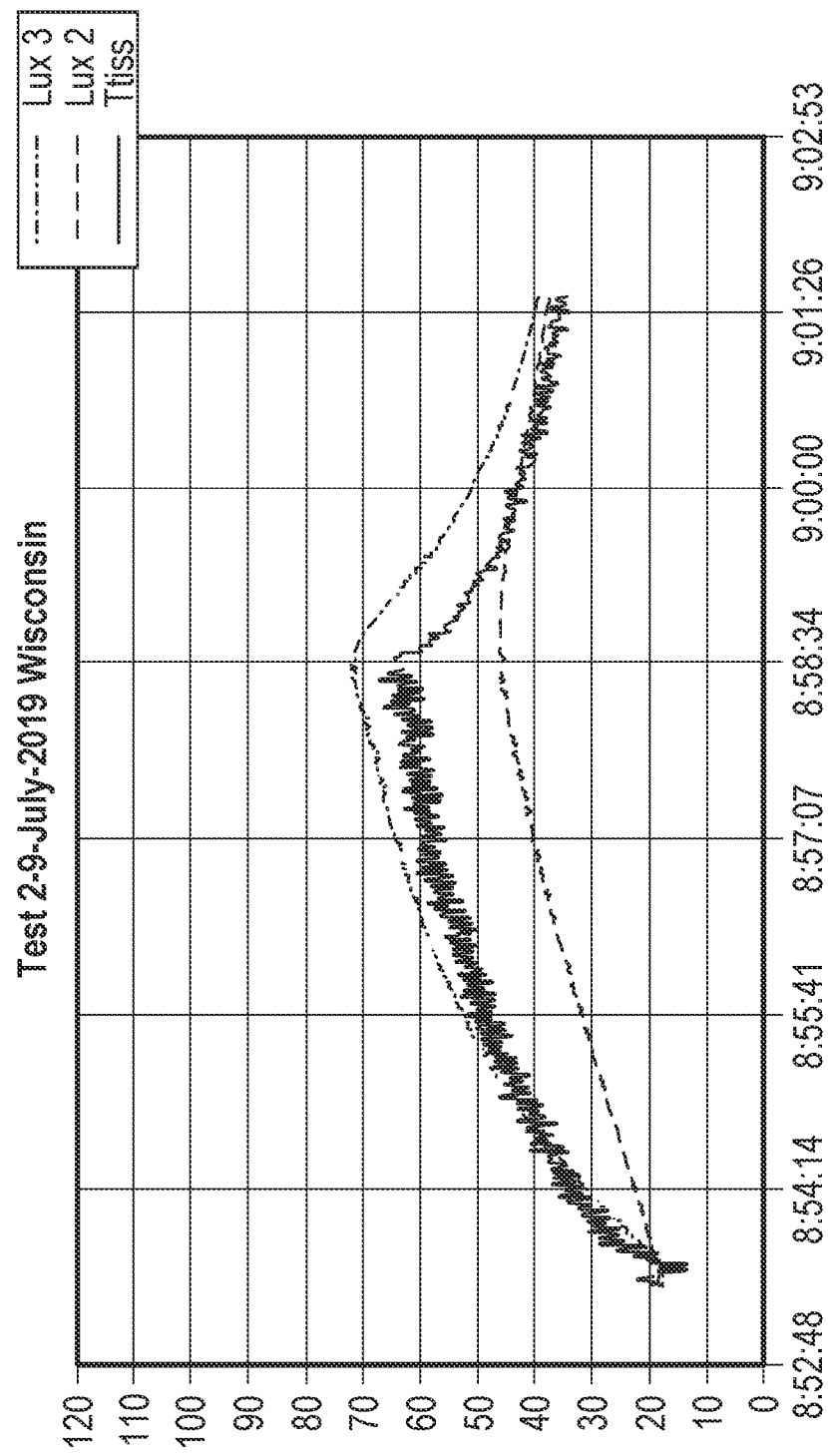
FIG. 17 is a graph illustrating temperature versus time of an ablation procedure conducted in accordance with the principles of the present invention.

Referring again to FIG. 14, at step 103, switching antenna 22 is positioned adjacent target tissue, e.g., lung tissue. At step 104, as described above, the process switches between permitting main antenna 43 to emit microwave energy and permitting main antenna 43 to measure radiometer temperature generated as a result of energy emission by main antenna 43 via the switching network of switching antenna 22 in an interleaving manner. At step 105, the processor switches between permitting main antenna 43 to measure radiometer temperature and permitting reference termination 42 to measure the reference temperature. For example, as described above, in one ablation cycle (which may be repeated as desired) main antenna 43 may emit microwave energy for over 90% of the ablation cycle to maximize power dissipation, and main antenna 43 and reference termination 42 may alternate and measure radiometer temperature and reference temperature, respectively, for the remainder of the ablation period of the ablation cycle. At step 106, the processor may calculate target tissue temperature based on the measure radiometer temperature and the measured reference temperature using the calibrated values described above to account for the effect of energy emission on reference termination 42 and for the effect of microwave energy emission on the environment adjacent the target tissue during energy emission via main antenna 43. For example, FIG. 17 is a chart illustrating the measured target tissue temperature during a period of microwave ablation.

Figure 18A:
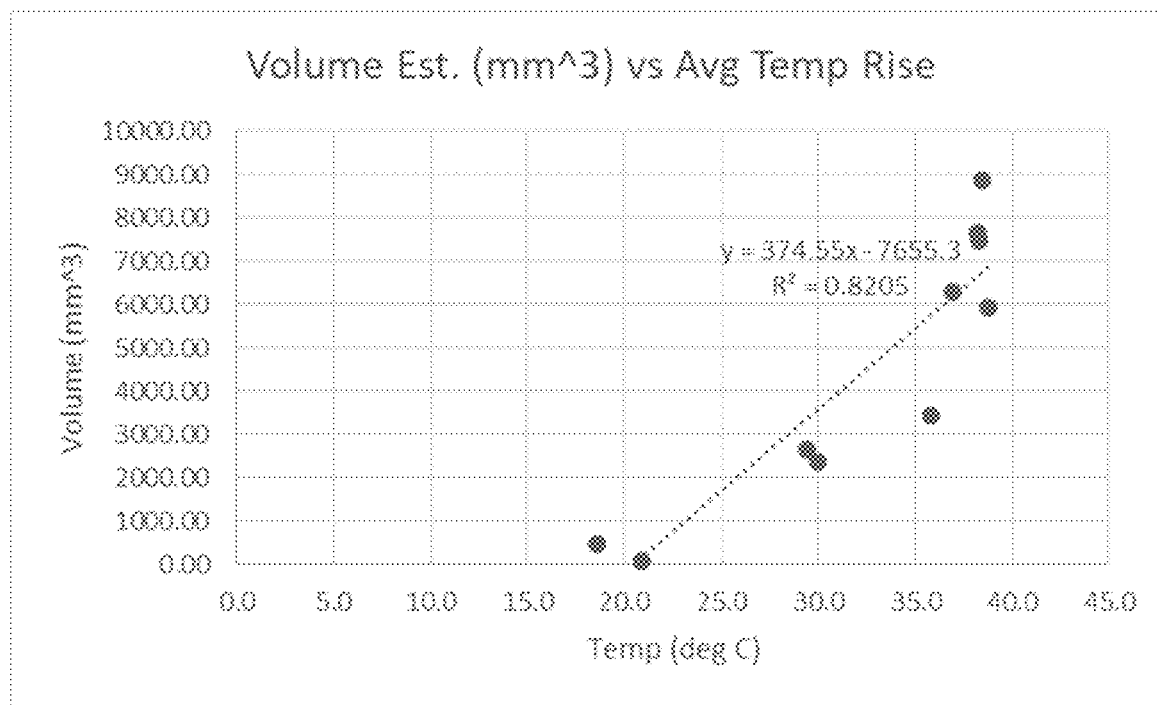
FIG. 18A is a graph illustrating ablation lesion volume versus average target tissue temperature of an ablation procedure conducted in accordance with the principles of the present invention.
Figure 18B:
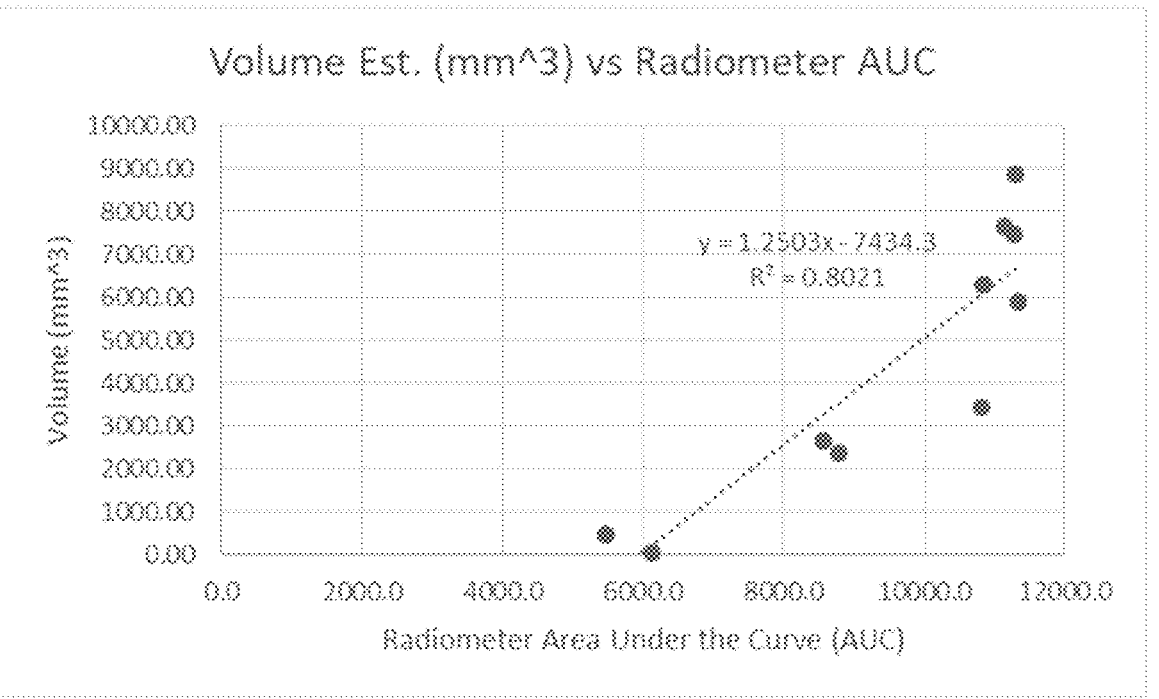
FIG. 18B is a graph illustrating ablation lesion volume versus radiometer area under the curve of target tissue temperature of an ablation procedure conducted in accordance with the principles of the present invention.

Referring again to FIG. 14, at step 107, the processor may estimate the volume of the ablation lesion resulting from the microwave energy emission via main antenna 43 during the ablation procedure based on the target tissue temperature. Specifically, the volume of the ablation lesion created by energy emission during an ablation procedure may be estimated based on at least one of an average target tissue temperature or an area under a plotted curve of the target tissue temperature. For example, FIG. 18A illustrates a graph plotting average target tissue temperature versus the estimated ablation lesion volume, and FIG. 18B illustrates a graph plotting the radiometer area under a plotted curve of target tissue temperature versus the estimated ablation lesion volume. Moreover, the estimated ablation lesion volume may be used to permit titration of the energy emission to achieved desired therapeutic goals.

Figure 19:
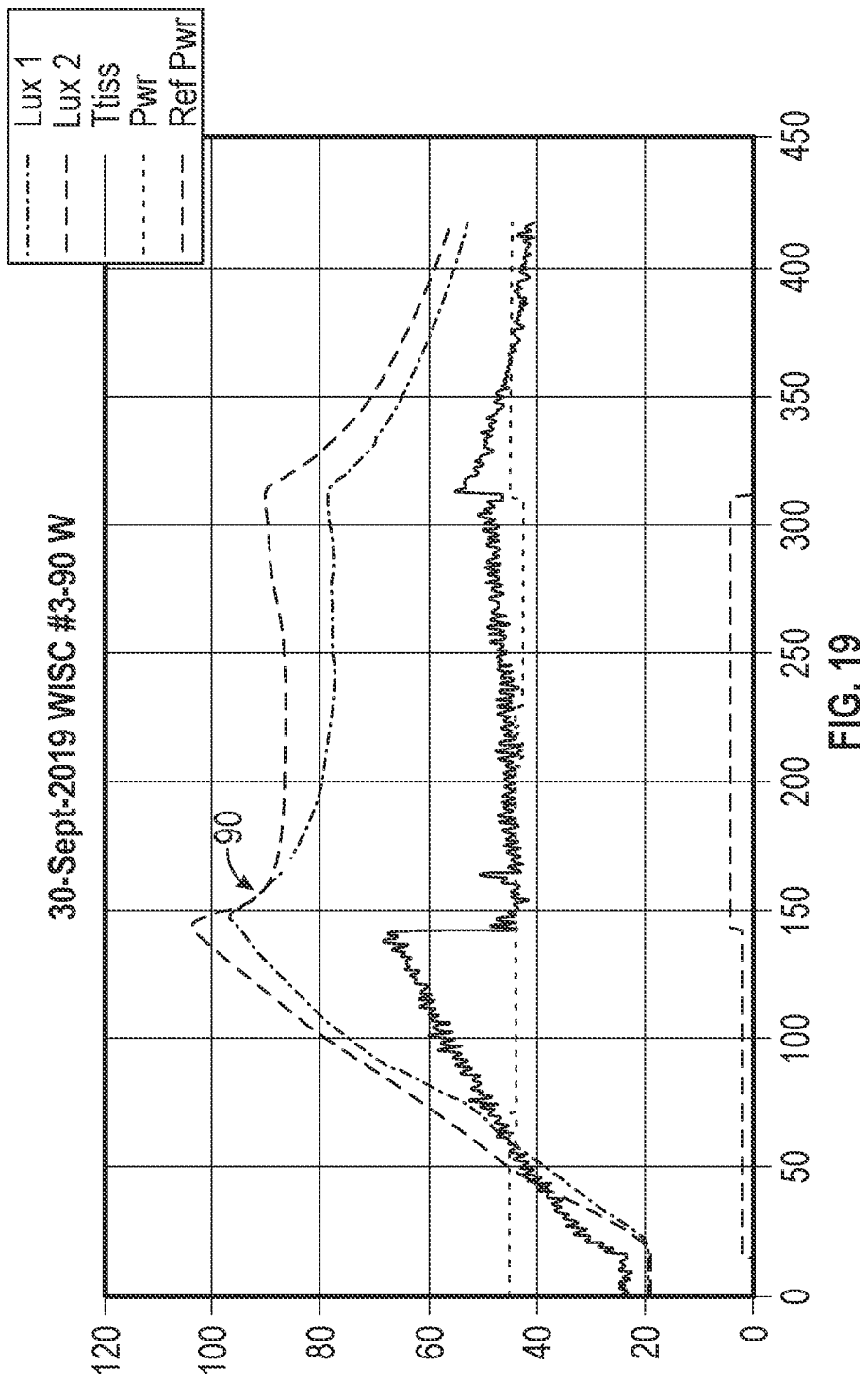
FIG. 19 is a graph illustrating a pop condition within target tissue temperature.

Referring now to FIG. 19, a pop condition, e.g., a steam pop, may be detected and/or predicted via algorithms programmed into the processor described above. As shown in FIG. 19, pop condition 90 is indicative of a rapid target tissue temperature rise followed by a sudden target tissue temperature drop. The sudden drop may be indicative of the switching antenna being moved out of location, and therefore no longer heating the target tissue. Accordingly, as the processor monitors the target tissue temperature in real time, the processor may be able to detect when the target tissue temperature is raising too quickly, or otherwise in a manner outside a predetermined threshold, and predict that a pop condition will be observed. When pop condition 90 is detected or predicted to occur, the processor may automatically cut off heating and/or generate an alert to alert the user that there is an issue.

Additionally or alternatively, the processor may be programmed to automatically modulate the energy emission via main antenna 22 in response to detection or prediction of a pop condition to thereby prevent over heating of the target tissue and/or other issues. For example, the energy emission via the main antenna may be modulated to reduce at least one of the target tissue temperature or a rate of increase of the target tissue temperature if the pop is predicted. Detecting and prediction of pop conditions improves the safety and efficacy of the ablation systems described herein. Moreover, the processor may be coupled to a display for displaying the monitoring of the target tissue temperature such that a user may visualize the pop condition within the target tissue temperature. In addition, the temperature may be controlled to a set temperature point by modulating the power to achieve a constant temperature.

Figure 20:
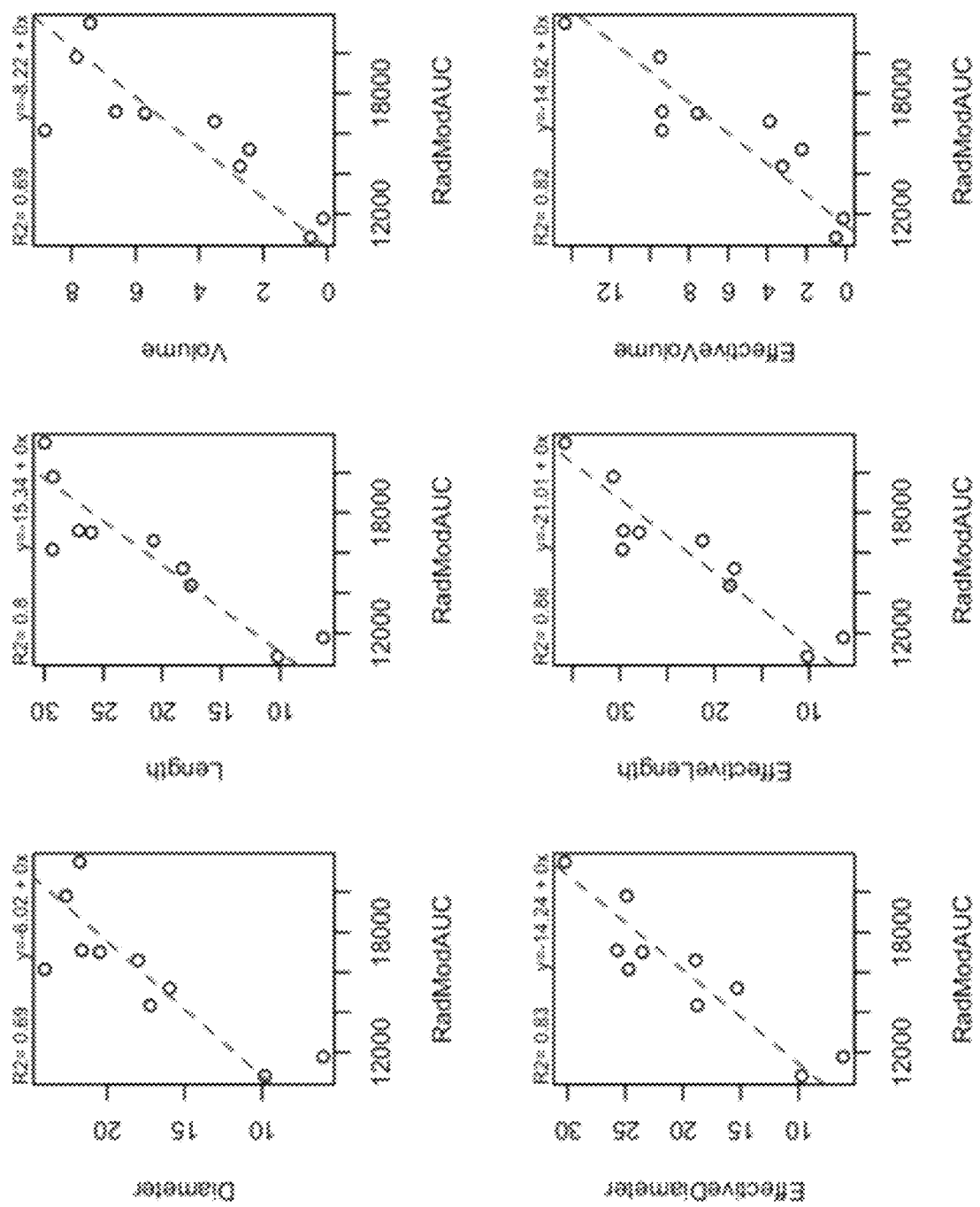
FIG. 20 illustrates data indicative of induced thermal lesions in homogenous tissue.

Clinical testing results discussed below confirm efficacy of the microwave heating and measurement systems described herein. For example, FIG. 20 illustrates data indicative of microwave ablation-induced thermal lesions in homogenous tissue.

Figure 21A:
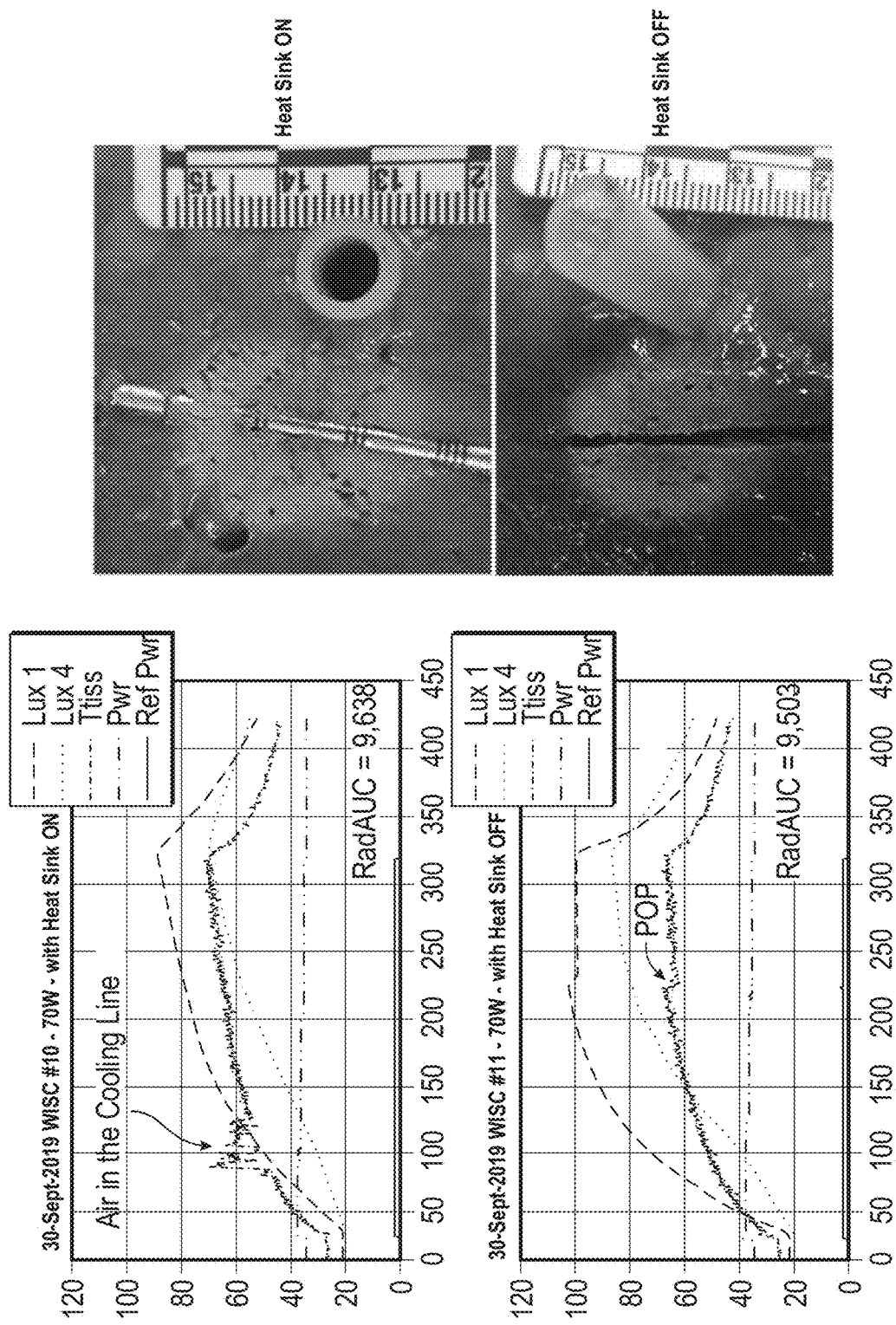
Figure 21C:
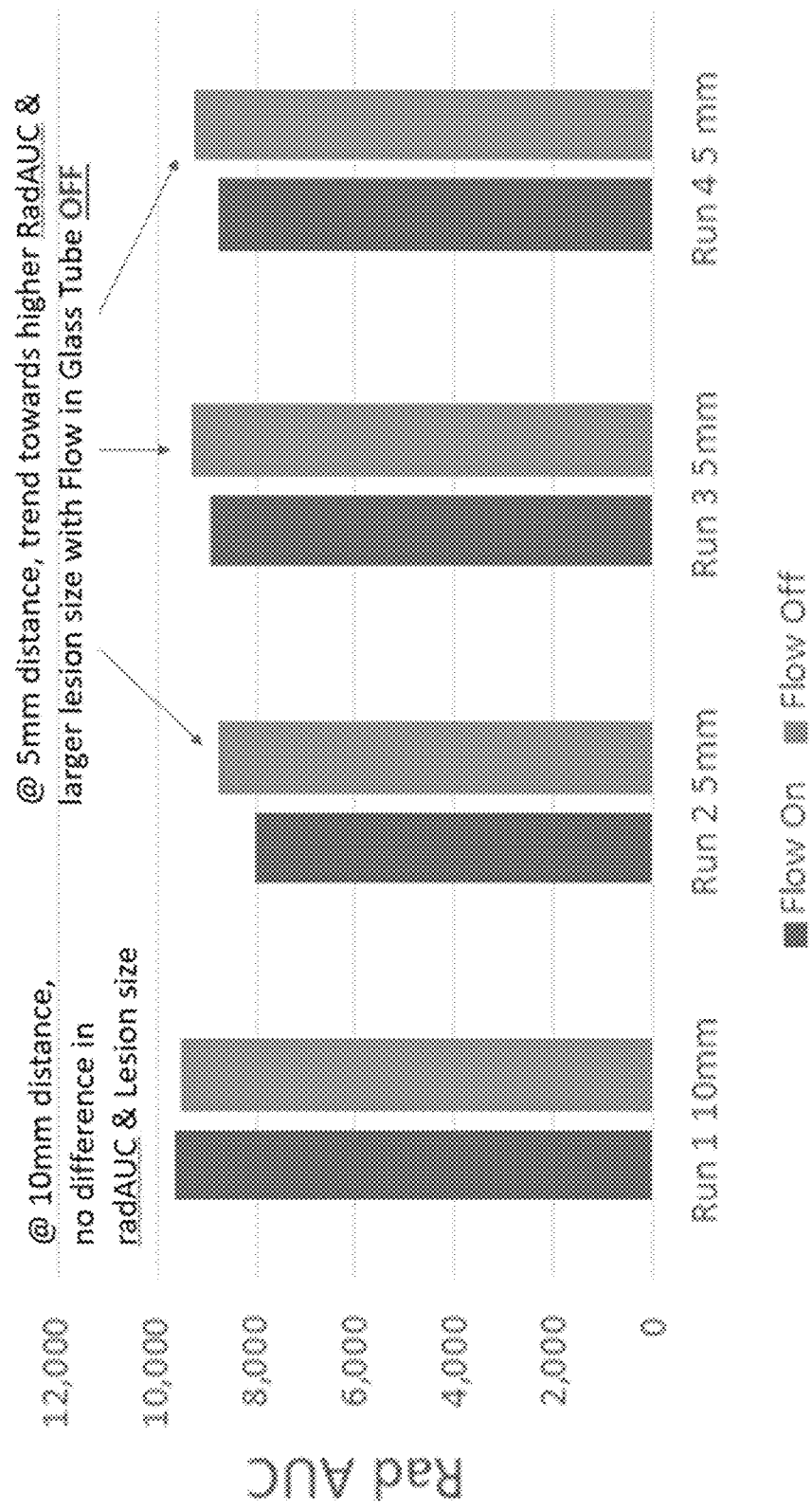

FIG. 21A-21C illustrate results of heat sink testing using an ablation system in accordance with the principles of the present invention. For example, a glass tube was positioned in the field of the ablation to draw away heat from the zone of heating. This would mimic a blood vessel. As shown in FIGS. 21A-21C, a lower radiometer area under the curve ("Rad AUC") is achieved when the flow in the tube (or heat sink) is on compared to when it is off. This correlates to a smaller lesion size. Accordingly, the volume of the lesion may be determined even when there is a heat sink, e.g., a blood vessel, pulling heat away from the ablation zone. Known methods only permit the user to control power and set the level of power and time, which does not allow the user to determine if the heat is effectively heating and destroying tissue. For example, the user cannot know if there are ten vessels pulling heat away (and making smaller lesions) or zero vessels pulling heat away. In accordance with the principles of the present invention, the user may more precisely predict lesion size in the presence of heat sinks such as blood vessels.

Figure 22:
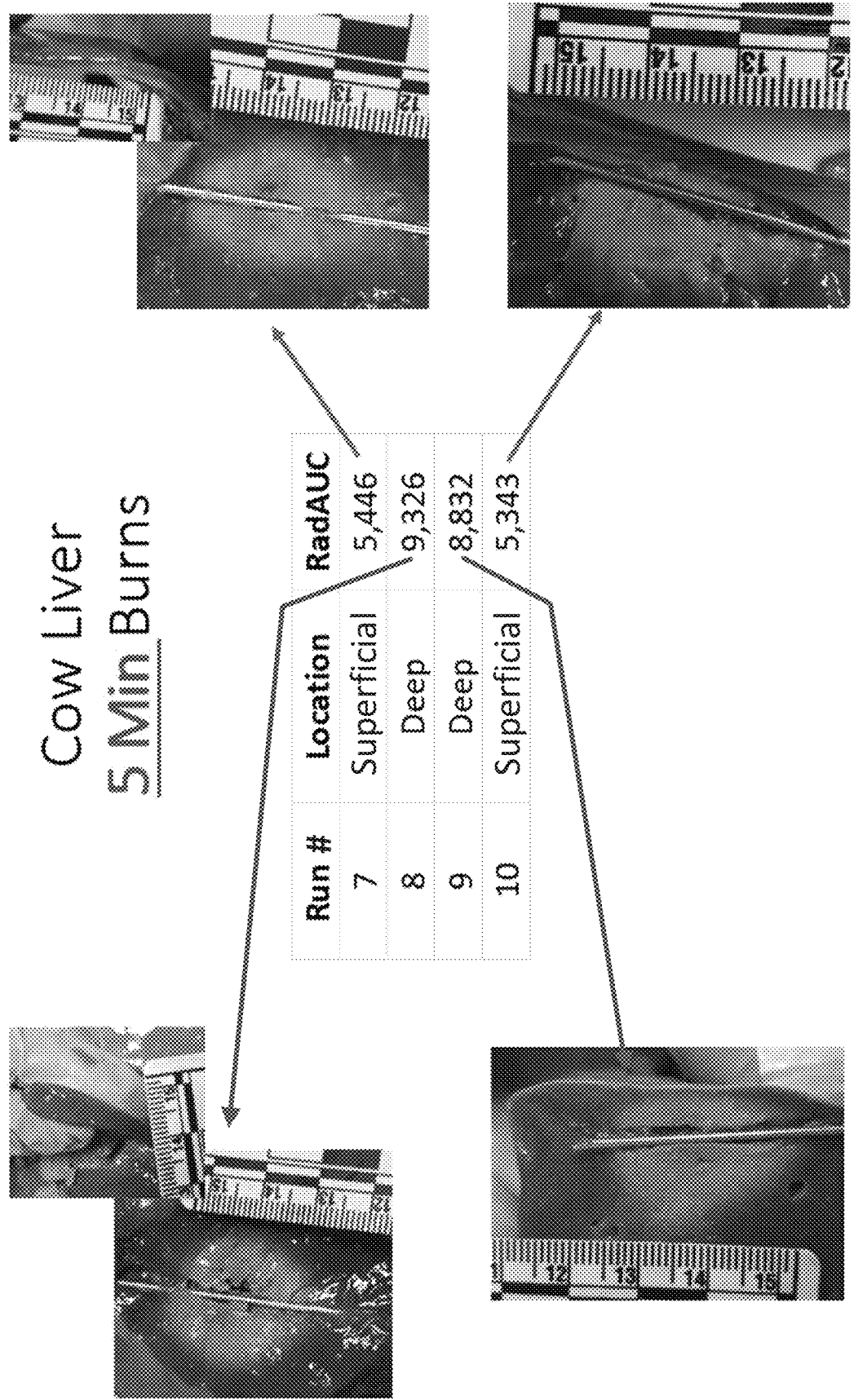
FIG. 22 illustrates results of heat sink testing on cow liver using an ablation procedure conducted in accordance with the principles of the present invention.

FIG. 22 illustrates results of heat sink testing on cow liver using an ablation procedure conducted in accordance with the principles of the present invention. Specifically, a more extreme example of a heat sink was simulated. The antenna was positioned just below the surface of the tissue and the tissue was positioned in a water bath. Accordingly, on one side, the antenna was seeing all tissue, and on the other side, the antenna was seeing less tissue and mostly water/saline. In addition, flow in the water was created to pull away the heat in the water as an extreme way of heat sinking. Here again, the radiometer could detect when there was a lot of heat sink with the antenna near the surface and the water pulling heat away (low AUC) and when there was no heat sink (fully embedded in tissue), and thus a higher heating and higher AUC.

Figure 23:
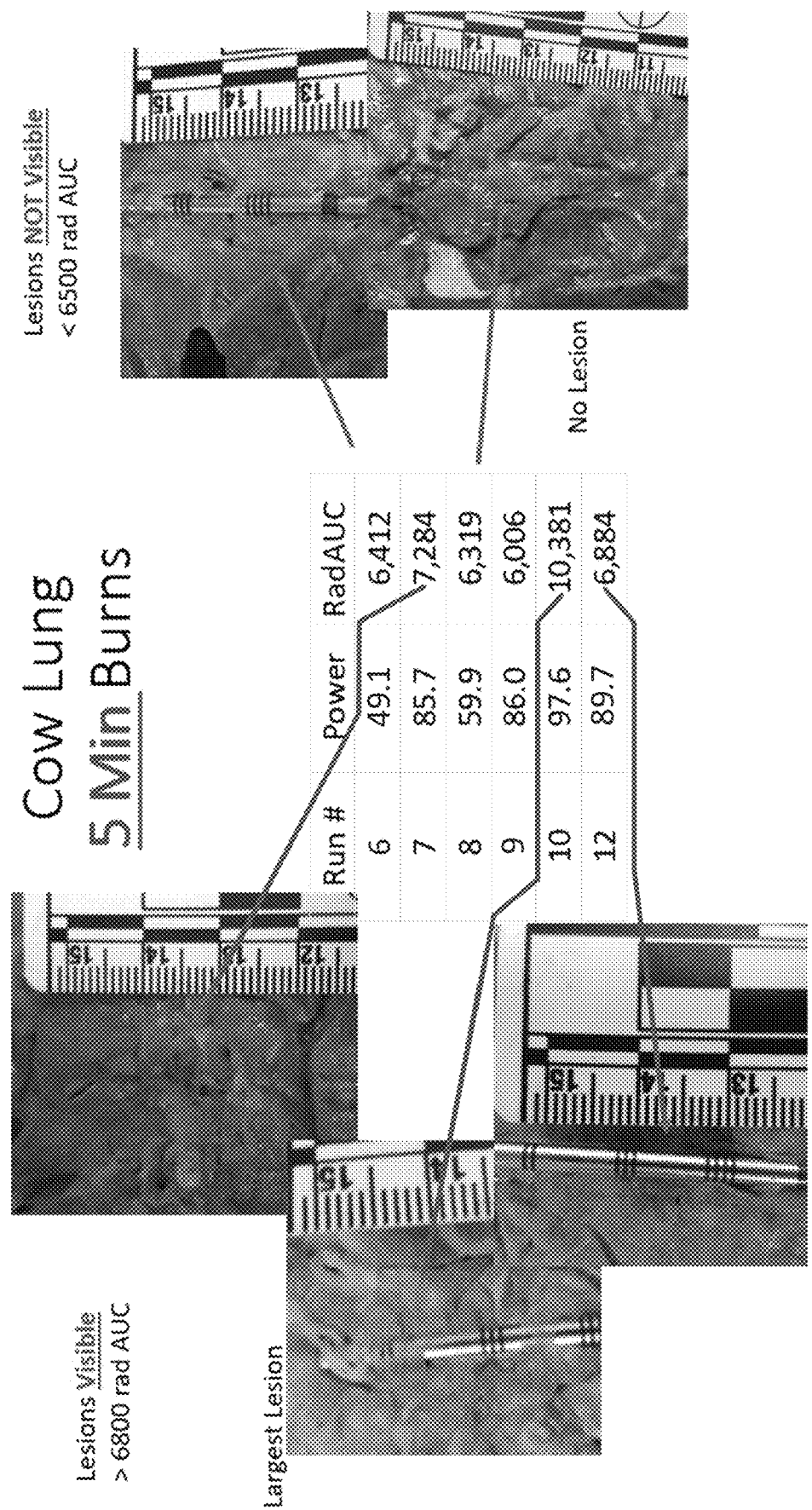
FIG. 23 illustrates results of lung ablation testing on cow liver using an ablation procedure conducted in accordance with the principles of the present invention.
Figure 24A:
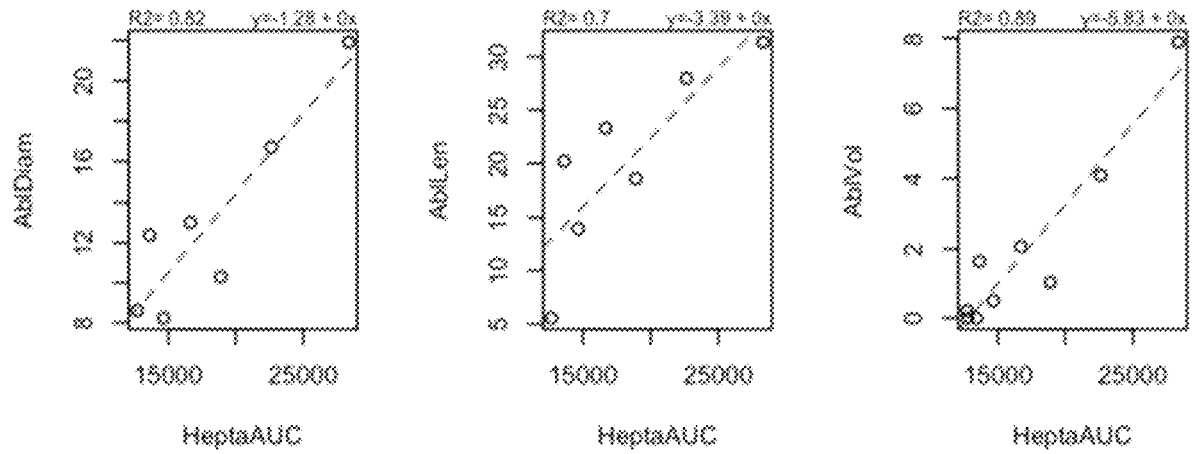
FIG. 24A illustrates data indicative of radiometer AUC resulting from lung ablation testing.
Figure 24B:
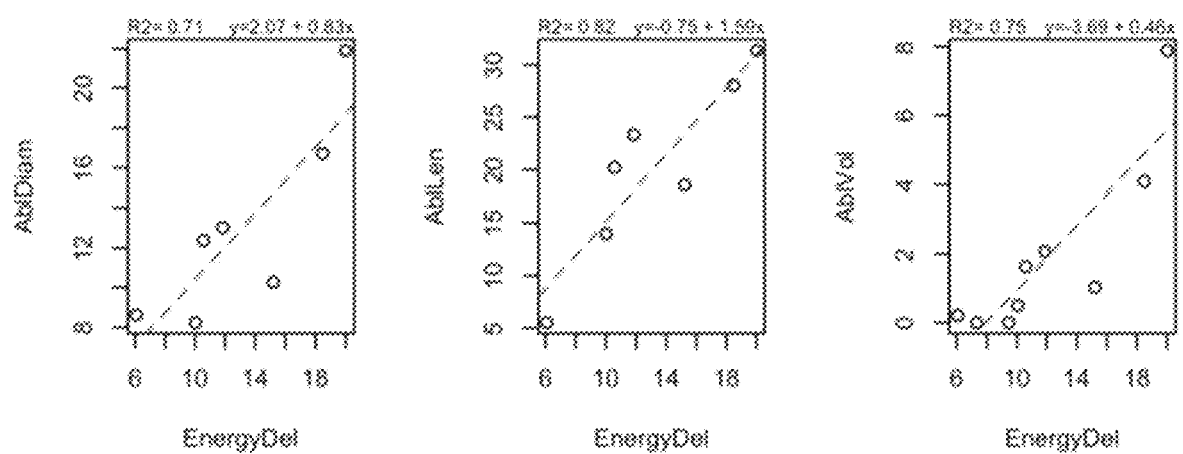
FIG. 24B illustrates data indicative of delivered energy resulting from lung ablation testing.

FIG. 23 illustrates results of lung ablation testing on cow liver using an ablation procedure conducted in accordance with the principles of the present invention. Compared to liver tissue discussed above, which is very homogenous, liver tissue is non-homogenous, e.g., having air pockets and connective tissue, etc. As shown in FIG. 23, microwave ablation systems constructed in accordance with the principles of the present invention may further be used on non-homogenous tissue to predict ablation lesion volume with a strong AUC correlation to lesion volume. Moreover, FIG. 24A illustrates data indicative of radiometer AUC resulting from lung ablation testing, and FIG. 24B illustrates data indicative of delivered energy resulting from lung ablation testing. Specifically, FIG. 24A illustrates regression plots of radiometer AUC versus diameter, length, and volume (from left to right), and FIG. 24B illustrates regression plots of delivered microwave energy versus diameter, length, and volume (from left to right).

Figure 25A:
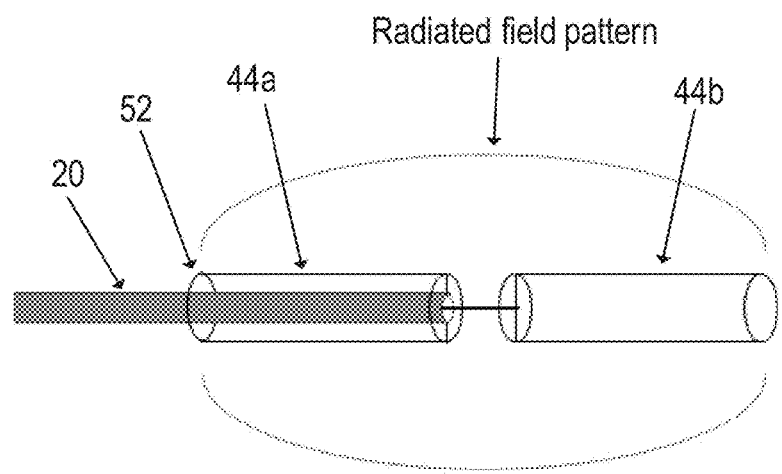
FIG. 25A illustrates a basic dipole of the microwave radiating elements of an exemplary microwave ablation system.

Referring now to FIG. 25A, a basic dipole of the microwave radiating elements of a switching antenna of an exemplary microwave ablation system is provided. Specifically, FIG. 25A illustrates a switching antenna constructed similar to switching antenna 22 of FIG. 5A with the switching network omitted for clarity. As shown in FIG. 25A, the switching antenna includes microwave radiating elements 44a, 44b forming two dipole halves of the switching antenna. As described above, microwave choke arrangement 52 at the proximal end of microwave radiating element 44a minimizes fold back of the radiating field pattern of microwave energy from microwave radiating elements 44a, 44b onto the coaxial catheter shaft. The choke is formed by connecting the proximal dipole half, e.g., microwave radiating element 44a, to cable 20 at the feed point of the switching antenna. A coaxial structure is formed between microwave radiating element 44a and cable 20 which results in the open circuit choke between the switching antenna and cable 20.

Figure 25B:
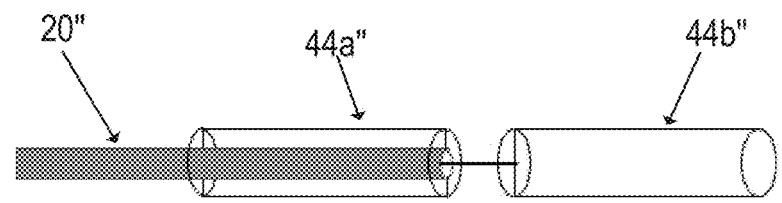
FIG. 25B illustrates conversion of the basic dipole of FIG. 25A into a monopole in accordance with the principles of the present invention.
Figure 25C:
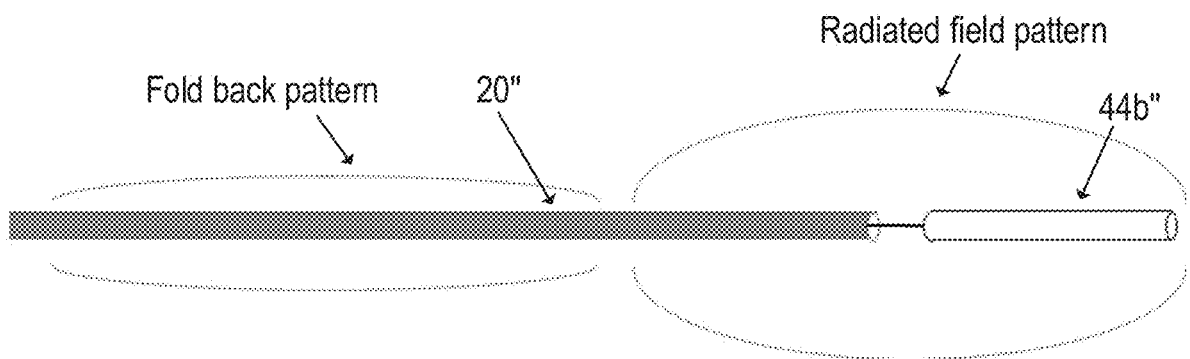
FIG. 25C illustrates a thin monopole constructed in accordance with the principles of the present invention.

As shown in FIG. 25B, the basic dipole of the switching antenna of FIG. 25A may be converted into a monopole by shorting the proximal end of microwave radiating element 44a" to defeat the choke action of microwave radiating element 44a". Accordingly, microwave radiating elements 44a" and 44b" may form a monopole. The monopole may have a similar diameter as cable 20" as shown in FIG. 25C, thereby providing an overall smaller diameter switching antenna. The radiation fold back pattern of the monopole may be tolerated as the smaller diameter device may be required for applications described herein.

Figure 26A:
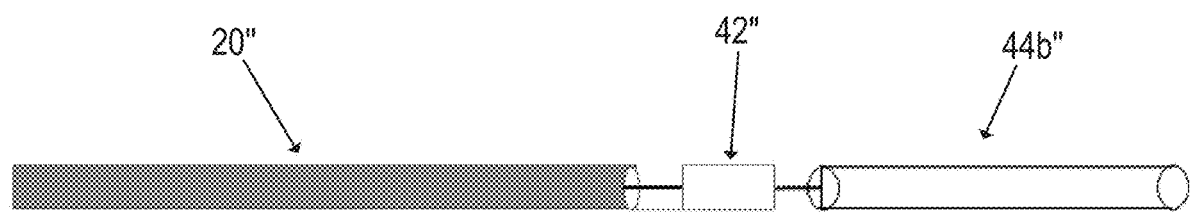
FIG. 26A illustrates an exemplary microwave ablation system where the switching network is disposed within the monopole in accordance with the principles of the present invention.
Figure 26B:
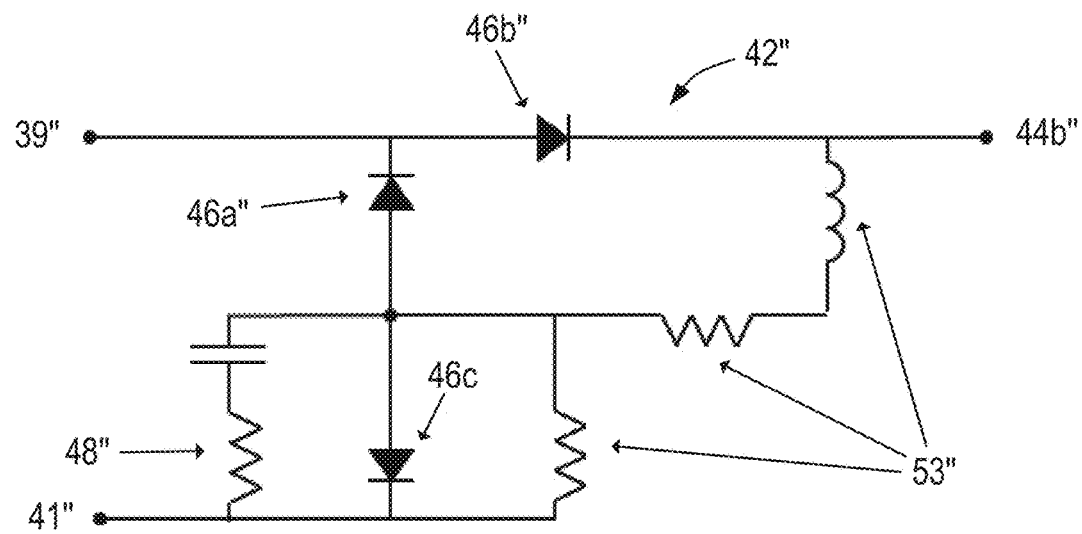
FIG. 26B illustrates the switching network of the microwave ablation system of FIG. 26A.

Referring now to FIG. 26A, the switching antenna of FIGS. 25B and 25C is illustrated with switching network 42" depicted. As shown in FIG. 26A, switching network 42" may be positioned at a junction between microwave radiating elements 44a", 44b". As shown in FIG. 26B, switching network 42" may be constructed similar to switching network 42 of FIG. 5B, except that switching network 42" may further include third switching diode 46c in addition to first switching diode 46a" and second switching diode 46b", as well as an additional bias component 53". Third switching diode 46c may improve isolation of reference termination 48" from the radiometer temperature, e.g., heating of tissue due to ablation, during ablation of the target tissue.

Figure 26C:
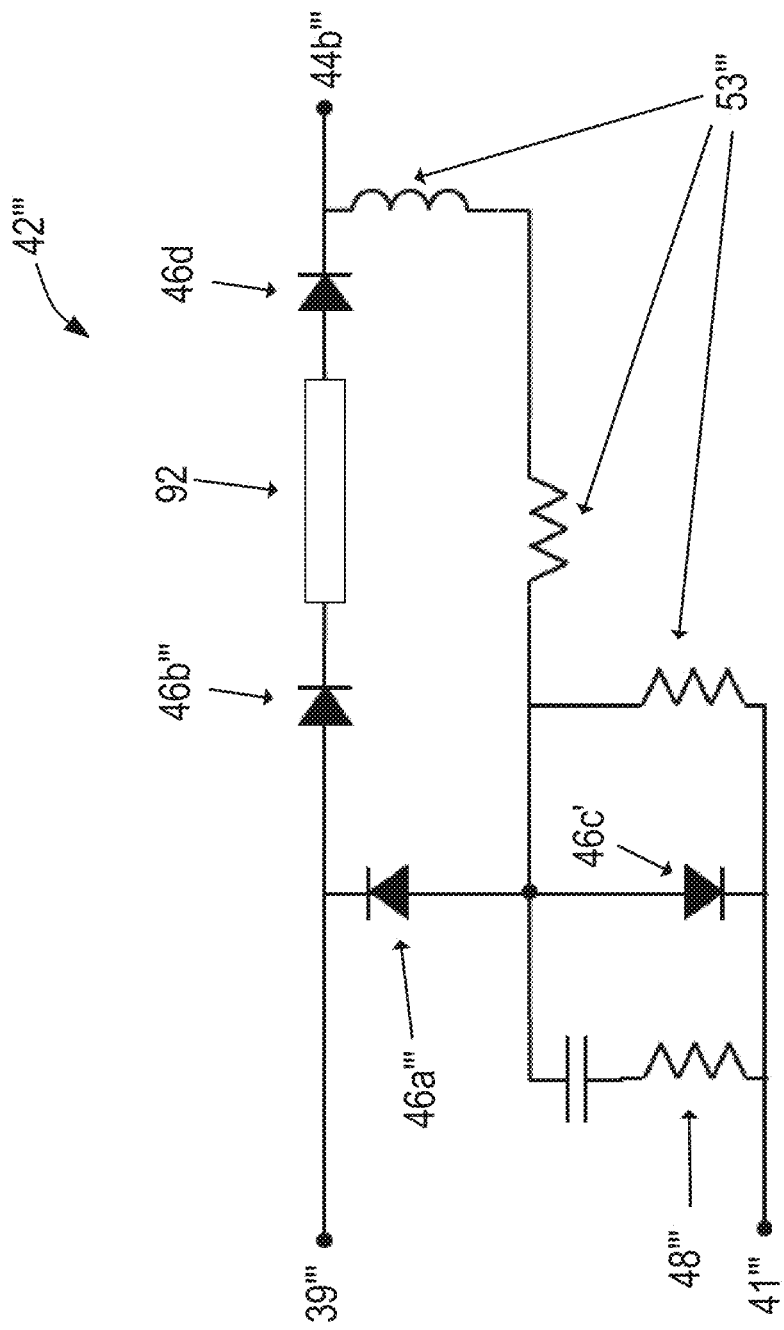
FIG. 26C illustrates an alternative switching network of the microwave ablation system of FIG. 26A.

Referring now to FIG. 26C, another alternative switching network is provided. Switching network 42'" includes fourth switching diode 46d, in addition to first switching diode 46a'", second switching diode 46b'", and third switching diode 46c'. Fourth switching diode 46d may improve isolation of reference termination 48'" from the radiometer temperature during measurement of the reference temperature. As shown in FIG. 26C, fourth switching diode 46d and second switching diode 46b'" may be in series with the main antenna, e.g., microwave radiating element 44b'", and separated by microstrip transmission line 92 on the switching network substrate. Microstrip transmission line 92 may improve the isolation achieved by the two switching diodes 46b'", 46d, which may be especially useful for applications using higher ablation frequencies. As will be understood by a person having ordinary skill in the art, switching network 42'" may replace switching network 42" in the switching antenna of FIG. 26A.

Referring now to FIGS. 27A and 27B, the switching antenna of FIG. 26A is illustrated with switching network 42" pushed back from the monopole tip to accommodate a smaller diameter coaxial cable, e.g., cable 20", at or near the main antenna, e.g., microwave radiating element 44b". As shown in FIG. 27A, switching network 42" may be pushed back into the distal region of cable 20", proximal to the proximal end of microwave radiating element 44b". Alternatively, as shown in FIG. 27B, switching network 42" may be pushed further back into the distal region of cable 20", e.g., at a point along cable 20" where cable 20" transitions from smaller diameter coaxial cable portion 20a" to larger diameter coaxial cable portion 20b". Specifically, as switching network 42" may be disposed within larger diameter coaxial cable portion 20b" of cable 20", further away from microwave radiating element 44b", cable 20" may include smaller diameter coaxial cable portion 20a" extending between microwave radiating element 44b" and switching network 42".

Switching network 42" may be disposed in switch module 130, which may be structured to be removeably coupled to a coaxial cable of a target device. As shown in FIG. 27B, switch module 130 may be removably coupled to a distal end of larger diameter coaxial cable portion 20b" of cable 20" via proximal connector 96 and to a proximal end of smaller diameter coaxial cable portion 20a" of cable 20" via distal connector 94, thereby providing an electrical connection between the generator and microwave radiating element 44b". As will be understood by a person having ordinary skill in the art, though FIG. 27B depicts cable portion 20b" having a larger diameter than cable portion 20a", cable portions 20a" and 20b" may have the same diameter, such that cable 20" may have a uniform diameter throughout.

Figure 28C:
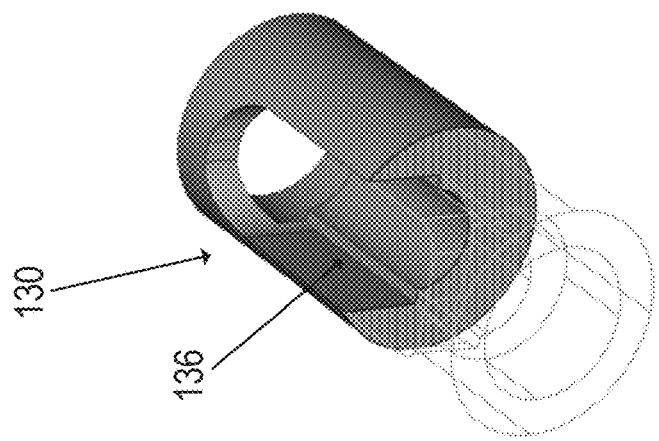
FIGS. 28A to 28C illustrate an exemplary switch module constructed in accordance with the principles of the present invention.
Figure 28B:
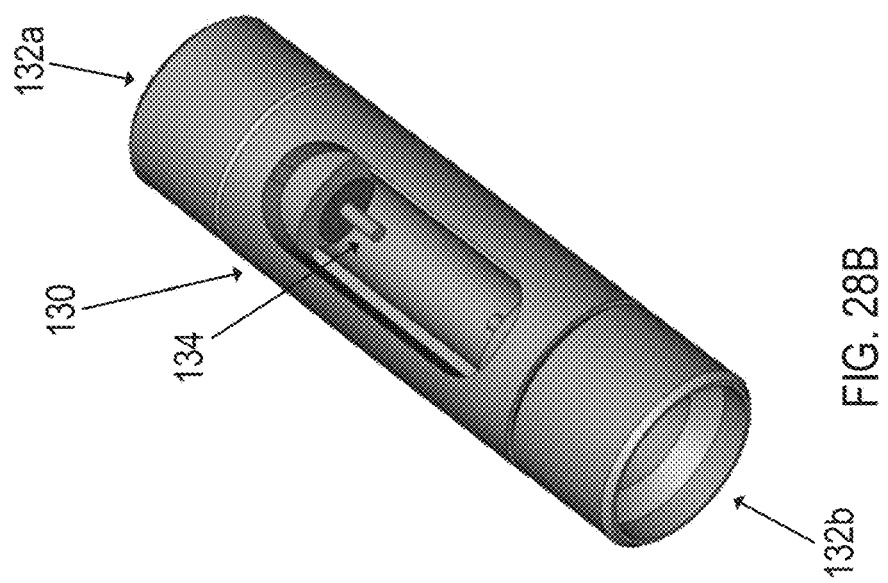
Figure 28A:
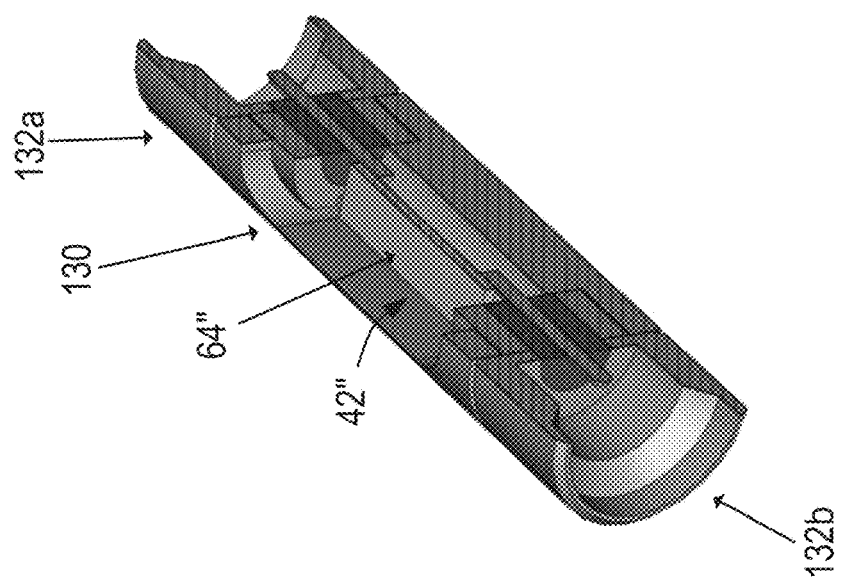

Referring now to FIGS. 28A to 28C, an exemplary switch module is provided. As shown in FIG. 28A, switch module 130 may include proximal connector 132a which may be electrically coupled with proximal connector 96, and distal connector 132b which may be electrically coupled with distal connector 94. For example, proximal connector 132a may have a lumen sized and shaped to receive a portion of proximal connector 96 such that proximal connector 132a and proximal connector 96 may be releasably engaged, and distal connector 132b may have a lumen sized and shaped to receive a portion of distal connector 94 such that distal connector 132b and distal connector 94 may be releasably engaged. Accordingly, switch module 130 may easily be integrated with an existing target device.

As shown in FIG. 28A, switching network 42" may be disposed on substrate 64", which may be disposed within switch module 130. For example, as shown in FIG. 28B, switch module 130 may include conductor 134, e.g., the center conductor of coaxial cable 20", to provide an electrical connection between cable 20" and substrate 64" within switch module 130. Moreover, as shown in FIG. 28C, switch module 130 further may include ledge 136 to provide support to substrate 64" within switch module 130.

Figure 29:
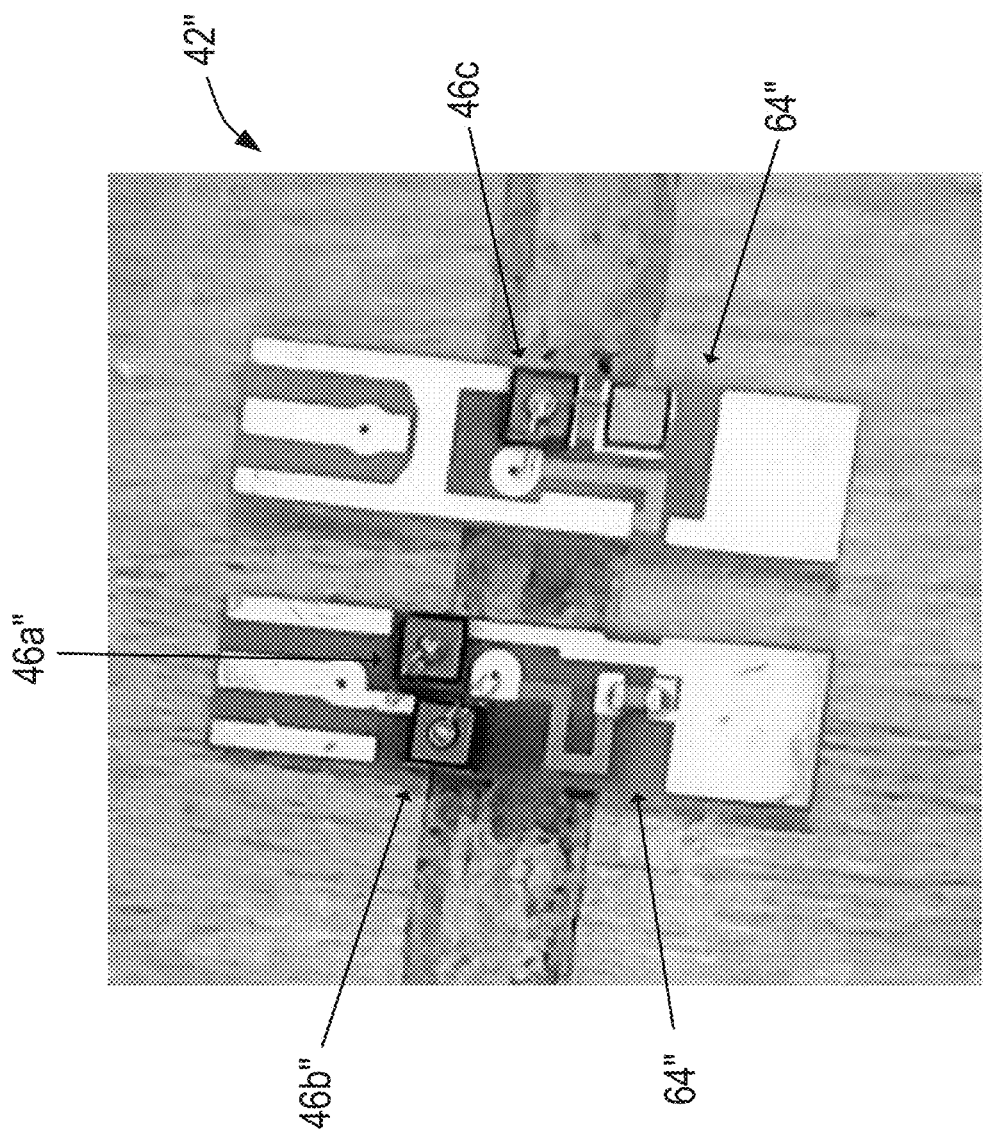
FIG. 29 illustrates an exemplary switch substrate constructed in accordance with the principles of the present invention.

Referring now to FIG. 29, switching network 42" of FIG. 26B is illustrated on substrate 64". As shown in FIG. 29, first switching diode 46a" and second switching diode 46b" may be disposed on a first side of substrate 64" (left photo), and third switching diode 46c may be disposed on an opposite side of substrate 64" (right photo).

While various illustrative embodiments of the invention are described above, it will be apparent to one skilled in the art that various changes and modifications may be made herein without departing from the invention. It will further be appreciated that the systems and methods described herein may be utilized for ablation and temperature measurements of tissue other than the renal artery. The appended claims are intended to cover all such changes and modifications that fall within the true spirit and scope of the invention.

What is claimed is:

1. A system for ablating target tissue within a patient, the system comprising:
a catheter having a proximal region and a distal region;
a switching antenna disposed at the distal region of the catheter, the switching antenna comprising a main antenna comprising a proximal radiating element, a distal radiating element, and a microwave choke arranged at a proximal end of the proximal radiating element configured to minimize fold back of a radiating field pattern along the main antenna, the main antenna configured to switch between emitting energy to ablate the target tissue and measuring a radiometer temperature generated as a result of the energy emission with a radiometer;
a reference termination disposed between the proximal radiating element and the distal radiating element, the reference termination comprising a temperature sensor configured to measure a reference temperature at the distal region;
a switch electrically coupled to the main antenna and the reference termination; and
a processor operatively coupled to the main antenna and the reference termination, the processor configured to:
selectively switch the main antenna to measure the radiometer temperature and the reference termination to measure the reference temperature in an alternating manner via the switch; and
calculate a target tissue temperature based on the measured radiometer temperature and the measured reference temperature,
wherein the switching antenna is configured to convert from a dipole antenna to a monopole antenna by shorting a proximal-most end of the proximal radiating element to the main antenna with a short to defeat a choke action of the proximal radiating element, thereby permitting an amount of fold back of the radiating field pattern of the energy emission along the catheter.

2. The system of claim 1, wherein the switch is configured to be disposed between the proximal radiating element and the distal radiating element.

3. The system of claim 1, wherein the switch is configured to be disposed within a proximal region of the proximal radiating element, the proximal region proximal to a junction between the proximal radiating element and the distal radiating element.

4. The system of claim 1, wherein the switch comprises first and second switching diodes.

5. The system of claim 4, wherein the switch comprises a third switching diode configured to improve isolation of the reference termination from the radiometer temperature during ablation of the target tissue.

6. The system of claim 5, wherein the switch comprises a fourth switching diode configured to improve isolation of the reference termination from the radiometer temperature during measurement of the reference temperature.

7. The system of claim 6, wherein the second switching diode and the fourth switching diode are in series with the main antenna, and separated by a microstrip transmission line.

8. The system of claim 1, further comprising a switch module configured to house the switch, the switch module comprising proximal and distal coaxial connectors configured to be removeably coupled to a coaxial cable of the catheter.

9. The system of claim 1, wherein the processor is further configured to estimate a volume of an ablation lesion created by the energy emission during an ablation procedure based on the target tissue temperature.

10. The system of claim 9, wherein the processor is further configured to permit titration of the energy emission based on the estimated volume of the ablation lesion.

11. The system of claim 1, wherein the processor is further configured to estimate a volume of an ablation lesion created by the energy emission during an ablation procedure based on at least one of an average of the target tissue temperature or an area under a plotted curve of the target tissue temperature.

12. The system of claim 1, wherein the processor is further configured to permit titration of the energy emission based on the target tissue temperature.

13. The system of claim 1, wherein the processor is further configured to selectively switch the main antenna to emit the energy and measure the radiometer temperature and the reference termination to measure the reference temperature in an interleaving manner.

14. The system of claim 13, wherein the processor is configured to selectively switch the main antenna to emit the energy for a first time period, and the main antenna to measure the radiometer temperature and the reference termination to measure the reference temperature in the alternating manner for a second time period.

15. The system of claim 14, wherein the first time period is at least 80% percent of a sum of the first and second time periods.

16. The system of claim 1, wherein the processor is further configured to modulate the energy emission such that the calculated target tissue temperature is maintained within a predetermined threshold.

17. The system of claim 1, wherein the processor is further configured to perform a reference termination calibration to account for heating of the reference termination during the energy emission via the main antenna and a radiometer calibration to account for heating of an environment adjacent the target tissue during the energy emission via the main antenna.

18. The system of claim 17, wherein the processor is further configured to calculate the target tissue temperature based on the measured radiometer temperature and the measured reference temperature while accounting for heating of the reference termination and the environment adjacent the target tissue during the energy emission via the main antenna.

19. The system of claim 1, further comprising a cooling sleeve disposed over at least the distal region of the catheter, the cooling sleeve coupled to a source of coolant and configured to permit the coolant to flow over the main antenna and the reference termination, thereby cooling the main antenna and the reference termination during pre-ablation calibration and during an ablation procedure.

20. The system of claim 1, wherein the main antenna is configured to emit the energy to ablate the target tissue at a lung.

21. A system for ablating target tissue within a patient, the system comprising:
  a catheter having a proximal region and a distal region;
  a switching antenna disposed at the distal region of the catheter, the switching antenna comprising a main antenna comprising a proximal radiating element, a distal radiating element, and a microwave choke arranged at a proximal end of the proximal radiating element configured to minimize fold back of a radiating field pattern along the main antenna, the main antenna configured to switch between emitting energy to ablate the target tissue and measuring a radiometer temperature generated as a result of the energy emission with a radiometer, the switching antenna configured to convert from a dipole antenna to a monopole antenna by shorting a proximal-most end of the proximal radiating element to the main antenna with a short to defeat a choke action of the proximal radiating element;
  a reference termination disposed between the proximal radiating element and the distal radiating element, the reference termination comprising a temperature sensor configured to measure a reference temperature at the distal region; and
  a processor programmed to:
    perform a reference termination calibration to account for heating of the reference termination responsive to the energy emission via the main antenna and a radiometer calibration to account for heating of an environment adjacent the target tissue during the energy emission via the main antenna; and
    calculate a target tissue temperature based on the measured radiometer temperature and the measured reference temperature while accounting for heating of the reference termination and the environment adjacent the target tissue responsive to the energy emission via the main antenna.

22. The system of claim 21, wherein the energy emission generates an amount of fold back of a radiating field pattern of the energy emission along the catheter.

23. The system of claim 21, wherein the main antenna is configured to emit the energy to ablate the target tissue at a lung.

24. A system for ablating target tissue within a patient, the system comprising:
  a catheter having a proximal region and a distal region;
  a switching antenna disposed at the distal region of the catheter, the switching antenna comprising a main antenna comprising a proximal radiating element, a distal radiating element, and a microwave choke arranged at a proximal end of the proximal radiating element configured to minimize fold back of a radiating field pattern along the main antenna, the main antenna configured to switch between emitting energy to ablate the target tissue and measuring a radiometer temperature generated as a result of the energy emission with a radiometer, the switching antenna configured to convert from a dipole antenna to a monopole antenna by shorting a proximal-most end of the proximal radiating element to the main antenna with a short to defeat a choke action of the proximal radiating element;
  a reference termination disposed between the proximal radiating element and the distal radiating element, the reference termination comprising a temperature sensor configured to measure a reference temperature at the distal region;
  a cooling sleeve disposed over at least the distal region of the catheter, the cooling sleeve coupled to a source of coolant and configured to permit the coolant to flow over the main antenna and the reference termination, thereby cooling the main antenna and the reference termination during pre-ablation calibration and during an ablation procedure; and
  a processor programmed to:
    apply a radiometer signal to the main antenna at a first known environment temperature and measure a first output voltage of the reference termination;
    apply the radiometer signal to the main antenna at a second known environment temperature and measure a second output voltage of the reference termination;
    compare the first and second output voltages with the first and second known environment temperatures to calibrate out an effect of the energy emission via the main antenna on an environment adjacent the main antenna; and
    calculate a target tissue temperature based on the measured radiometer temperature and the measured reference temperature while accounting for heating of the environment adjacent the target tissue during the energy emission via the main antenna,
  wherein the cooling sleeve is configured to cool the reference termination to maintain a constant temperature of the reference termination at both the first and second known environment temperatures.

25. The system of claim 24, wherein the energy emission generates an amount of fold back of a radiating field pattern of the energy emission along the catheter.

26. The system of claim 24, wherein the main antenna is configured to emit the energy to ablate the target tissue at a lung.

* * * * *